US011969595B2

(12) United States Patent
Koka et al.

(10) Patent No.: US 11,969,595 B2
(45) Date of Patent: Apr. 30, 2024

(54) SYSTEMS AND METHODS FOR DETECTING ELECTRODE LEAD PROXIMITY TO COCHLEAR TISSUE

(71) Applicant: Advanced Bionics AG, Staefa (CH)

(72) Inventors: Kanthaiah Koka, Valencia, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 151 days.

(21) Appl. No.: 17/833,572

(22) Filed: Jun. 6, 2022

(65) Prior Publication Data
US 2022/0296898 A1 Sep. 22, 2022

Related U.S. Application Data

(63) Continuation of application No. 16/972,407, filed as application No. PCT/US2018/038345 on Jun. 19, 2018, now Pat. No. 11,376,431.

(51) Int. Cl.
*A61N 1/36* (2006.01)
*A61N 1/02* (2006.01)
(Continued)

(52) U.S. Cl.
CPC ......... *A61N 1/36039* (2017.08); *A61N 1/025* (2013.01); *A61N 1/0541* (2013.01);
(Continued)

(58) Field of Classification Search
CPC .. A61N 1/36039; A61N 1/025; A61N 1/0541; A61N 1/08; A61N 1/37211;
(Continued)

(56) References Cited

U.S. PATENT DOCUMENTS

| 5,649,970 A | 7/1997 | Loeb et al. |
| 6,195,585 B1 | 2/2001 | Karunasiri et al. |

(Continued)

FOREIGN PATENT DOCUMENTS

| WO | 2014105059 | 7/2014 |
| WO | 2015168388 | 11/2015 |

(Continued)

OTHER PUBLICATIONS

"International Search Report and Written Opinion received in International Application No. PCT/US2018/038345 on May 24, 2018."

(Continued)

*Primary Examiner* — Carl H Layno
*Assistant Examiner* — Anh-Khoa N Dinh
(74) *Attorney, Agent, or Firm* — ALG Intellectual Property, LLC

(57) ABSTRACT

An illustrative proximity detection system directs a first electrode of an electrode lead to apply a first pulse and directs a second electrode of the electrode lead to apply a second pulse concurrently with the first pulse so as to form a dipole that generates a field. The first and second electrodes are each configured as stimulating electrodes that apply stimulation to the cochlear tissue when the electrode lead is located at a resting position subsequent to a surgical insertion of the electrode lead into a cochlea of a patient. After the pulses are applied, and based on an energy magnitude of the field that is detected to reflect from cochlear tissue located within the field, the proximity detection system determines a proximity of the electrode lead to the cochlear tissue. Corresponding systems and methods are also disclosed.

20 Claims, 10 Drawing Sheets

(51) Int. Cl.
*A61N 1/05* (2006.01)
*A61N 1/08* (2006.01)
*A61N 1/372* (2006.01)

(52) U.S. Cl.
CPC .......... *A61N 1/08* (2013.01); *A61N 2001/083* (2013.01); *A61N 1/37211* (2013.01)

(58) Field of Classification Search
CPC .......... A61N 2001/083; A61N 1/36038; A61B 5/24; A61B 5/6886; A61B 5/4851; A61B 5/6815; A61B 5/063; A61B 5/38; A61B 2562/043; A61B 5/068; A61B 5/125; A61B 5/388; A61B 5/4836; A61B 5/6814; A61B 5/6817; A61B 5/743; A61B 8/0841; H01B 13/0036; H01B 3/46; H01B 7/048; G16H 40/63; H04R 2225/67; H04R 25/30; H04R 25/606
See application file for complete search history.

(56) References Cited

U.S. PATENT DOCUMENTS

| | | | |
|---|---|---|---|
| 8,532,781 | B1 | 9/2013 | Vanpoucke |
| 9,119,008 | B2 | 8/2015 | Johnston et al. |
| 9,597,495 | B2 | 3/2017 | Greenberg et al. |
| 9,597,503 | B2 | 3/2017 | Risi et al. |
| 2014/0350640 | A1 | 11/2014 | Patrick et al. |
| 2015/0049888 | A1* | 2/2015 | Johnston ............ A61N 1/36038 381/312 |
| 2015/0314122 | A1 | 11/2015 | Kabot et al. |
| 2015/0320550 | A1 | 11/2015 | Downing et al. |
| 2017/0367733 | A1 | 12/2017 | Murphy et al. |
| 2018/0280687 | A1 | 10/2018 | Carter |

FOREIGN PATENT DOCUMENTS

| | | |
|---|---|---|
| WO | 2017060832 | 4/2017 |
| WO | 2017131675 | 8/2017 |

OTHER PUBLICATIONS

Giardina, et al.,"Impedance Measures during in vitro Cochlear Implantation predict Array Positioning", DOI 10.1109/TBME.2017. 2764881, IEEE Transactions on Biomedical Engineering. vol. 65, Issue: 2, Feb. 2018. pp. 327-335.

Holden, et al., Factors Affecting Open-Set Word Recognition in Adults with Cochlear Implants, Ear Hear. 2013; 34(3): 342-360.

Long, et al., "Examining the Electro-Neural Interface of Cochlear Implant Users Using Psychophysics, CT Scans, and Speech Understanding", Journal of the Association for Research in Otolaryngology : JARO, (2014).

Mittmann, et al.,"Intraoperative electrophysiologic variations caused by the scalar position of cochlear implant electrodes", Otology & Neurotology, vol. 36, pp. 1010-1014, 2015.

O'Connell, et al., "Electrode Location and Audiologic Performance After Cochlear Implantation: A Comparative Study Between Nucleus CI422 and CI512 Electrode Arrays", Otology & Neurotology 37:1032-1035. 2016, Otology & Neurotology, Inc.

Suesserman, et al.,"Quantitative In Vivo Measurements of Inner Ear Tissue Resistivities: I. In Vitro Characterization", IEEE Transactions on Biomedical Engineering, 40(10), 1032-1047. Oct. 1993.

* cited by examiner

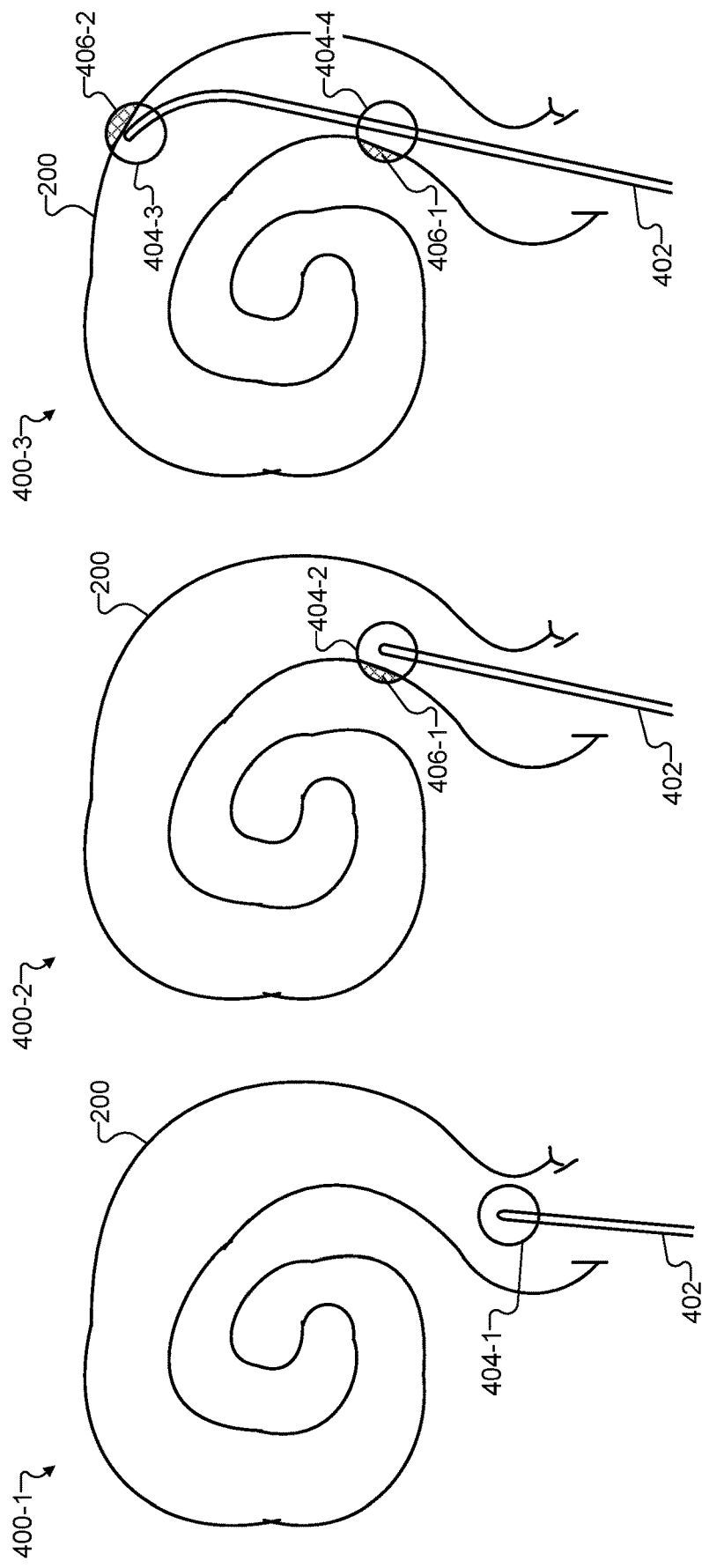

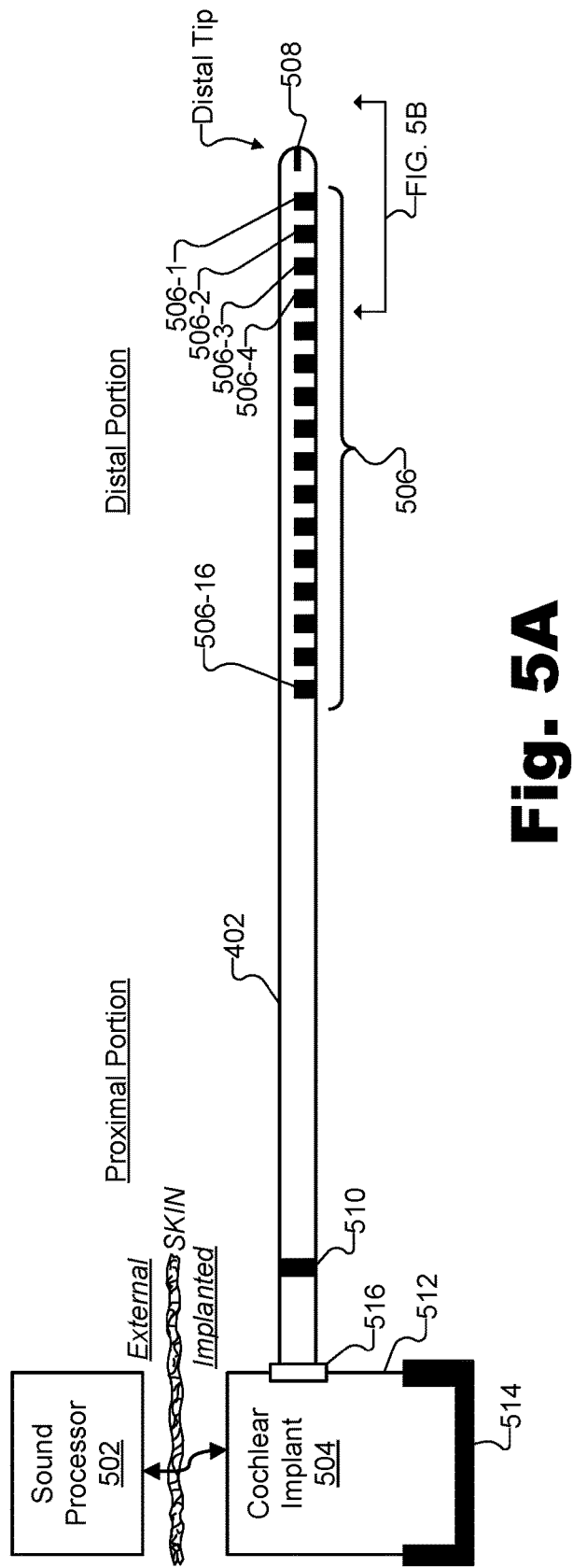
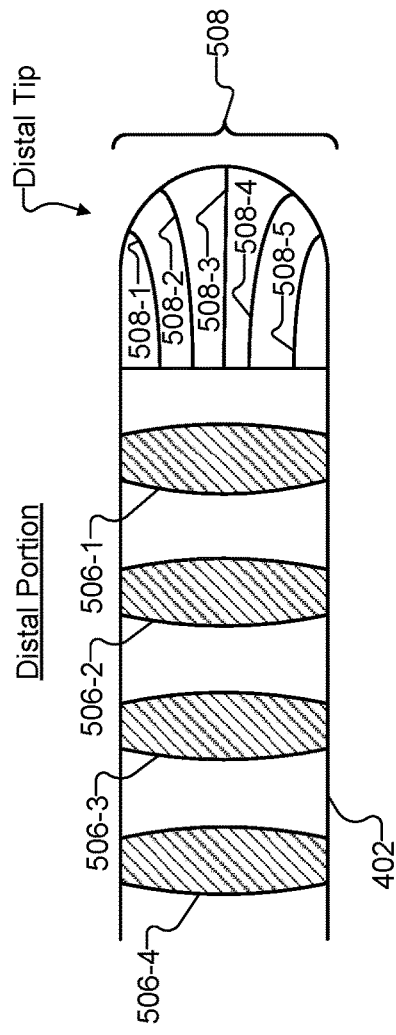
Fig. 5A
Fig. 5B

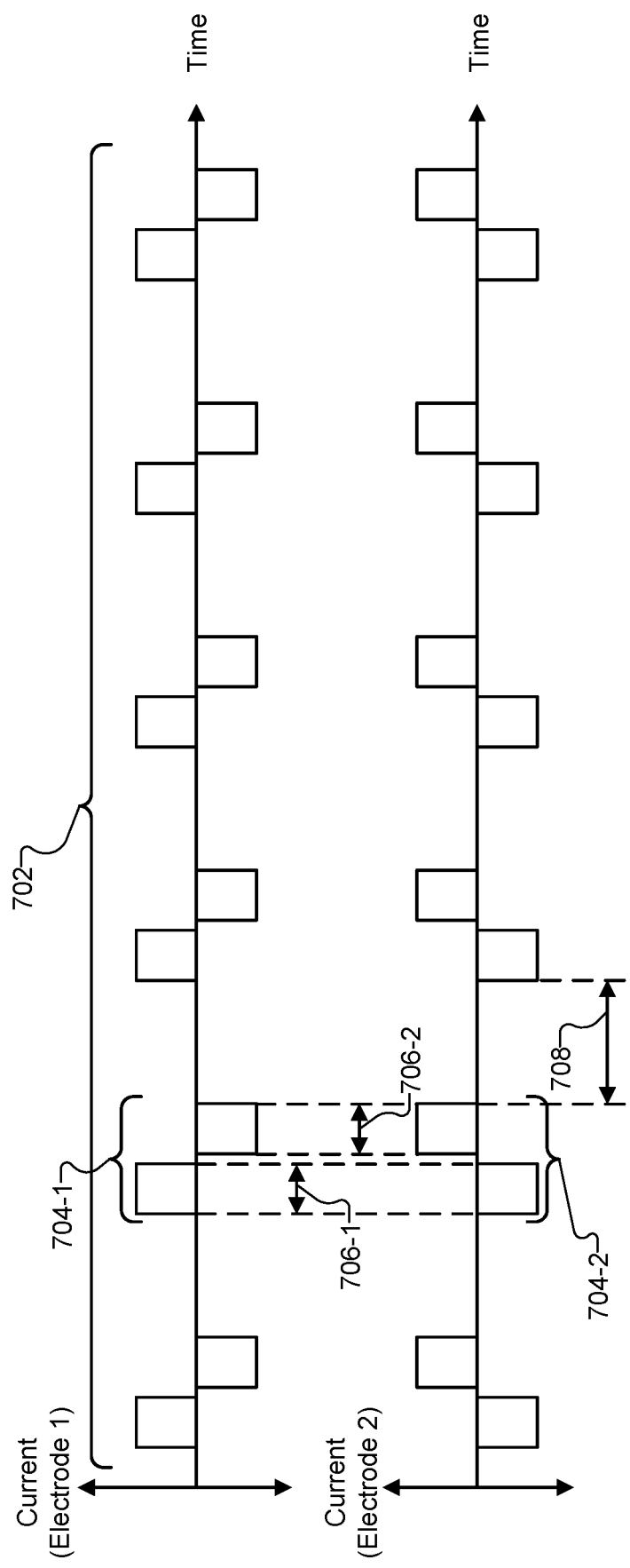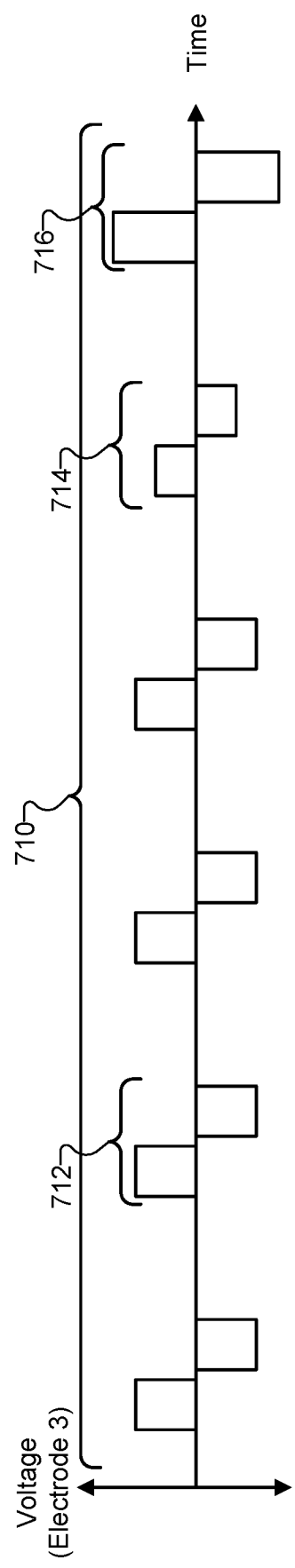
Fig. 7A
Fig. 7B

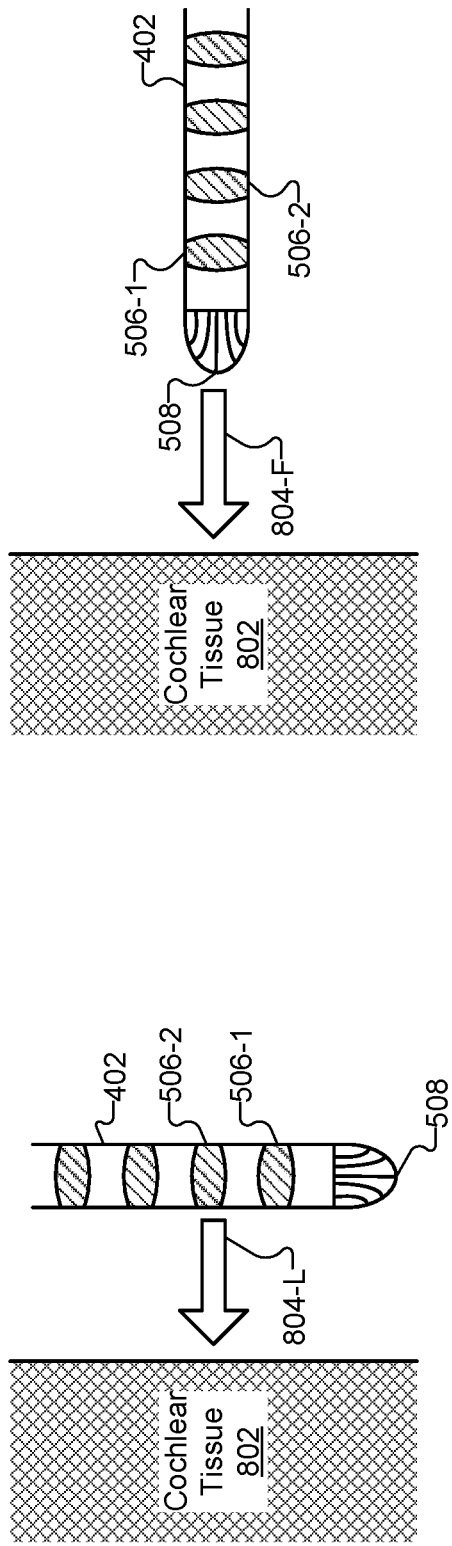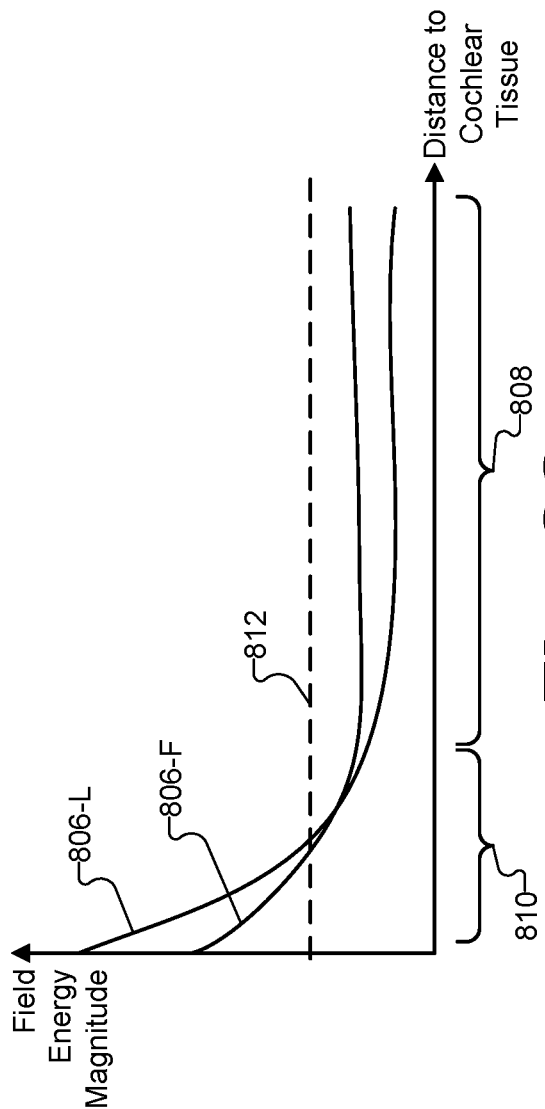

SYSTEMS AND METHODS FOR DETECTING ELECTRODE LEAD PROXIMITY TO COCHLEAR TISSUE

RELATED APPLICATIONS

This application is a continuation application of U.S. patent application Ser. No. 16/972,407, now U.S. Pat. No. 11,376,431 B2, filed Dec. 4, 2020, which is a U.S. National Stage Application under 35 U.S.C. § 371 of International Application No. PCT/US2018/038345, filed on Jun. 19, 2018, each of which is hereby incorporated by reference in its entirety.

BACKGROUND INFORMATION

Cochlear implant systems are used to provide, restore, and/or improve hearing loss suffered by cochlear implant patients who use the cochlear implant systems. A key component of a cochlear implant system is an electrode lead that is inserted into a cochlea of the patient in a delicate surgical procedure referred to herein as an "insertion procedure." Because insertion procedures are difficult and may result in cochlear trauma or other harm if not done with extreme care, surgeons may desire to carefully monitor and track the electrode lead and its position with respect to the cochlea both during and after the insertion procedure. For example, by periodically determining a proximity of the electrode lead to cochlear tissue, the surgeon or surgical team may more easily and conveniently perform a safe, effective surgical insertion of the electrode lead, thereby resulting in desirable hearing outcomes for patients.

Unfortunately, certain current techniques for determining electrode lead proximity with respect to cochlear tissue typically involve imaging technology (e.g., x-ray technology, fluoroscopic technology, CT scanning technology, etc.) that is expensive, inconvenient, and may expose patients to undesirable risk. Other current techniques involve acoustic stimulation (e.g., measuring evoked responses to electrocochleographic stimulation) that may be ineffective for patients who lack residual hearing ability. Accordingly, there remains room for improvement in developing systems and methods that detect electrode lead proximity to cochlear tissue safely, conveniently, inexpensively, and/or universally for all cochlear implant patients.

U.S. Patent Application No. 2015/0320550A1 ("Downing") discloses tip elements for cochlear implants. For example, Downing discloses a cochlear implant system including an electrode array comprising a tip element and a sensing module in communication with the tip element, in which the sensing module detects conditions surrounding the electrode array using the tip element during insertion of the electrode array into a cochlea.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 4A through 4C illustrate exemplary aspects of detecting an electrode lead proximity to cochlear tissue during an exemplary insertion procedure according to principles described herein.

FIG. 5A illustrates an exemplary electrode lead within an exemplary cochlear implant system according to principles described herein.

FIG. 5B illustrates an alternative view of a distal portion of the electrode lead of FIG. 5A according to principles described herein.

FIG. 7A illustrates exemplary pulses that are applied concurrently at first and second electrodes to have substantially equal magnitude and opposite phase according to principles described herein.

FIG. 7B illustrates exemplary detected pulses representative of energy magnitudes of fields generated by dipoles formed by the application of the pulses illustrated in FIG. 7A according to principles described herein.

FIGS. 8A and 8B illustrate exemplary movements of the electrode lead toward exemplary cochlear tissue according to principles described herein.

FIG. 8C illustrates an exemplary graph depicting field energy magnitude detected as a function of the proximity of the electrode lead to the cochlear tissue for the movements depicted in FIGS. 8A and 8B according to principles described herein.

DETAILED DESCRIPTION

Figure 1:
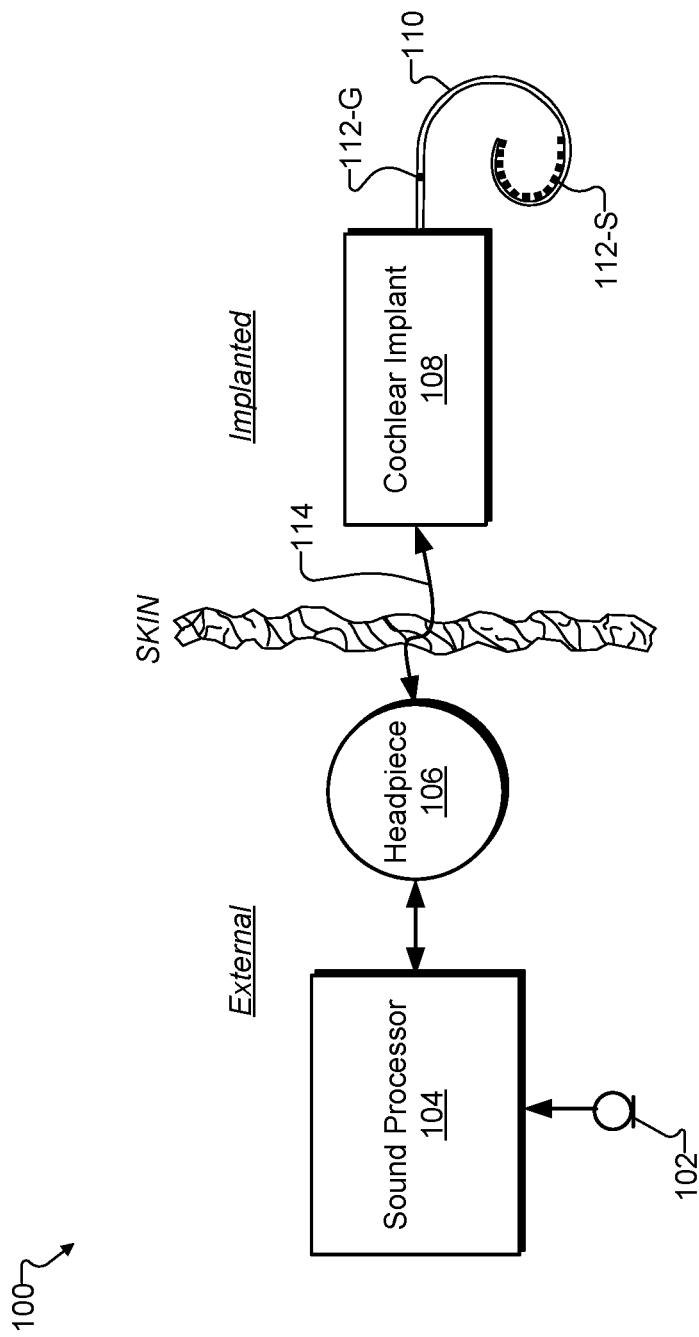
FIG. 1 illustrates an exemplary cochlear implant system according to principles described herein.

Systems and methods for detecting electrode lead proximity to cochlear tissue are described herein. For instance, in certain implementations, such systems and/or methods (referred to herein as "proximity detection systems" and/or "proximity detection methods") may be implemented and/or performed by a sound processor included in a cochlear implant system associated with a patient. Along with the sound processor, the cochlear implant system may further include a cochlear implant that is electrically coupled to an electrode lead having a plurality of electrodes disposed thereon and configured to be inserted into a cochlea of the patient. The sound processor may be configured to direct the cochlear implant to apply a first pulse by way of a first electrode disposed on the electrode lead, and to apply, concurrently with the application of the first pulse, a second pulse by way of a second electrode disposed on the electrode lead. The second pulse may have a substantially equal magnitude and an opposite phase to the first pulse such that the application of the first and second pulses forms a dipole that generates a field.

The sound processor may further be configured to direct the cochlear implant to detect an energy magnitude of the field that reflects from cochlear tissue located within the field. For instance, the cochlear implant may be directed by the sound processor to detect the energy magnitude by way of a third electrode disposed on the electrode lead (i.e., a separate electrode from the first and second electrodes that collectively cause the dipole to be formed and the field to be generated). Based on a difference between the detected energy magnitude of the field and a baseline energy magnitude of the field, the sound processor may be configured to determine a proximity of the electrode lead to the cochlear tissue.

In other implementations, proximity detection systems and/or methods disclosed herein may be implemented and/or performed in other ways and/or in other contexts. Specifically, in addition to being used in the context of cochlear implants and lead insertion procedures, proximity detection systems and/or methods disclosed herein may be used in other situations involving insertion of various objects into different types of cavities in which visibility is poor and progress is difficult to track. For example, certain types of catheters, endoscopic instruments, leads, or the like may be inserted into various places in the human body or into other hard to reach areas for a variety of medical or other purposes. If, in these examples, the objects being inserted include electrodes that may be used to form dipoles and/or detect fields, the proximity detection systems and/or methods disclosed herein may be employed to facilitate the insertion in a similar manner as described herein in relation to the insertion of an electrode lead into a cochlea during a cochlear implant insertion procedure. Various examples of proximity detection systems and methods will be described in more detail below.

Proximity detection systems and methods described herein may provide various benefits and advantages as compared to conventional systems and methods for monitoring an electrode lead location with respect to a cochlea of a patient. For example, while various techniques have been employed to intraoperatively or postoperatively determine a depth of an electrode lead that is being (or has been) inserted into a patient's cochlea, such techniques typically fail to reveal any information about a proximity of the electrode lead to the cochlear tissue. As such, surgeons using such conventional techniques may gain insight into how far the electrode lead has advanced into the cochlea, what turns within the cochlea the electrode lead may presently be navigating, and so forth. However, with only the information provided related to the insertion depth, these surgeons may still lack information regarding how close the electrode lead is to the walls of the cochlea.

In contrast, proximity detection systems and methods described herein may provide information (e.g., real-time information) regarding electrode proximity to cochlear tissue that may be valuable in addition to or instead of the information related to the insertion depth. For example, upon detecting that the electrode lead is approaching the cochlear tissue (regardless of a current insertion depth of the electrode lead), proximity detection systems described herein may indicate this information to surgeons and surgical teams. This may allow insertion procedures to be adapted (e.g., in real time) to be safer and/or otherwise more effective by allowing a surgeon to steer the electrode lead to avoid unwanted contact with the cochlear tissue, to back up and correct the approach of the electrode lead during the insertion procedure, to proceed with extra caution in further inserting the electrode lead, or the like. As a result, risks related to electrode lead translocations from one scala of the cochlea to another and/or other types of cochlear trauma may be reduced, thereby benefitting both surgeons and patients.

Another exemplary advantage of the proximity detection systems and methods described herein is that these systems and methods may be effective for all patients (e.g., including those who do not have residual hearing ability) and may be implemented and/or performed without additional equipment (e.g., imaging equipment, stimulation generation equipment, etc.) that may be costly, inconvenient or difficult to set up, and so forth. For example, while systems and methods that measure evoked responses to acoustic stimulation (e.g., electrocochleographic responses, etc.) require that a patient have at least some residual hearing ability, the proximity detection systems and methods described herein may be effective both for patients with and without residual hearing ability. Moreover, while systems that employ imaging technology to allow surgeons to view a proximity of an electrode lead to cochlear tissue may require the set up inconvenience and cost of various types of imaging equipment, the proximity detection systems and methods described herein may employ only the components of the cochlear implant system (e.g., the electrode lead, the cochlear implant, the sound processor, etc.) without any need for additional imaging or acoustic stimulation generation equipment.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary cochlear implant system 100. As shown, cochlear implant system 100 may include a microphone 102, a sound processor 104, a headpiece 106, a cochlear implant 108, and an electrode lead 110 that includes a plurality of electrodes 112 (e.g., stimulating electrodes 112-S and ground electrode 112-G) disposed thereon. As shown, electrode lead 110 may be pre-curved so as to properly fit within the spiral shape of the cochlea. Additional or alternative components may be included within cochlear implant system 100 as may serve a particular implementation.

As shown, cochlear implant system 100 may include various components configured to be located external to a patient including, but not limited to, microphone 102, sound processor 104, and headpiece 106. Cochlear implant system 100 may further include various components configured to be implanted within the patient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a clinician's programming interface ("CPI") device, etc.) to one or more stimulation sites associated with an auditory pathway such as the auditory nerve of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, headpiece 106, and/or any other sound processing unit as may serve a particular implementation).

As will be described in more detail below, sound processor 104 may further direct cochlear implant 108 to generate and/or apply pulses (e.g., electrical pulses, current pulses, optical pulses, magnetic pulses, etc.) that, unlike the stimulation current described above, are not meant to be perceived by the patient directly. For example, by directing cochlear implant 108 to generate equal and opposite phase pulses in the manner described herein, sound processor 104 may cause a dipole (e.g., an electric dipole, a magnetic dipole, an optical dipole, etc.) to be formed that generates a field that may be used to detect electrode lead proximity to cochlear tissue in accordance with the systems and methods described herein.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil disposed in or physically coupled to cochlear implant 108). Communication link 114 may include a bi-directional communication link and/or one or more dedicated uni-directional communication links as may serve a particular implementation.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via communication link 114.

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the patient via electrodes 112 disposed along electrode lead 110. For example, an array of stimulating electrodes 112-S (also referred to as intracochlear electrodes) disposed on a distal portion of electrode lead 110 may be configured to be located within and to stimulate the cochlea after the distal portion of electrode lead 110 is inserted into the cochlea. At least one ground electrode 112-G (also referred to as a ring electrode) may be disposed on a proximal portion of electrode lead 110 and configured to provide, in certain configurations, a current return path for stimulation current generated by electrodes 112-S. As such, ground electrode 112-G may typically be configured to remain external to the cochlea after electrode lead 110 is inserted into the cochlea. While a single ground electrode 112-G is shown in FIG. 1, it will be recognized that multiple ground electrodes 112-G may be disposed on the proximal portion of electrode lead 110 as may serve a particular implementation.

In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112. Additionally, as mentioned above, cochlear implant 108 may be directed to apply pulses (e.g., current pulses similar to the stimulation current) that may not be configured to be perceived by the patient, but may instead serve other purposes such as facilitating the detecting of electrode lead proximity to cochlear tissue in the ways described herein.

In some examples, at least one computing device (e.g., a programming system or the like, not shown in FIG. 1) that is separate from cochlear implant system 100 may be communicatively coupled to sound processor 104 in order to facilitate proper insertion of electrode lead 110 into a cochlea of a patient during a surgical insertion procedure, to perform one or more programming or fitting operations with respect to cochlear implant system 100, or for other suitable purposes as may serve a particular implementation. As such, an external computing device of this type may implement, be included within, be communicatively coupled to, and/or be configured to control any of the proximity detection systems described herein.

For example, during an insertion procedure, an external computing device may direct sound processor 104 to perform operations for detecting the electrode lead proximity to the cochlear tissue within the patient. Additionally, subsequent to the insertion procedure, the external computing device may be used to present audio clips to the patient by way of cochlear implant system 100 in order to facilitate evaluation of how well cochlear implant system 100 is performing for the patient. In other examples, any of these operations may be performed by components of cochlear implant system 100 (e.g., by sound processor 104) without interaction with an external computing device.

An external computing device coupled with cochlear implant system 100 may be implemented by any suitable combination of physical computing and communication devices including, but not limited to, a fitting station or device, a programming device, a personal computer, a laptop computer, a handheld device, a mobile device (e.g., a mobile phone), a CPI device, and/or any other suitable component as may serve a particular implementation. In some examples, the computing device may provide one or more user interfaces with which a user may interact. For example, a user interface may provide text, graphics, sounds, etc., to facilitate a successful insertion procedure of electrode lead 110 or effective programming of sound processor 104 as may serve a particular implementation. In some implementations, the user interface may include a graphical user interface ("GUI") that allows a user (e.g., a surgeon, a person assisting the surgeon during an insertion procedure, a clinician, etc.) to direct the computing device to perform operations described herein and/or to provide information determined by a proximity detection system by way of visual or audible feedback as may serve a particular implementation.

Figure 2:
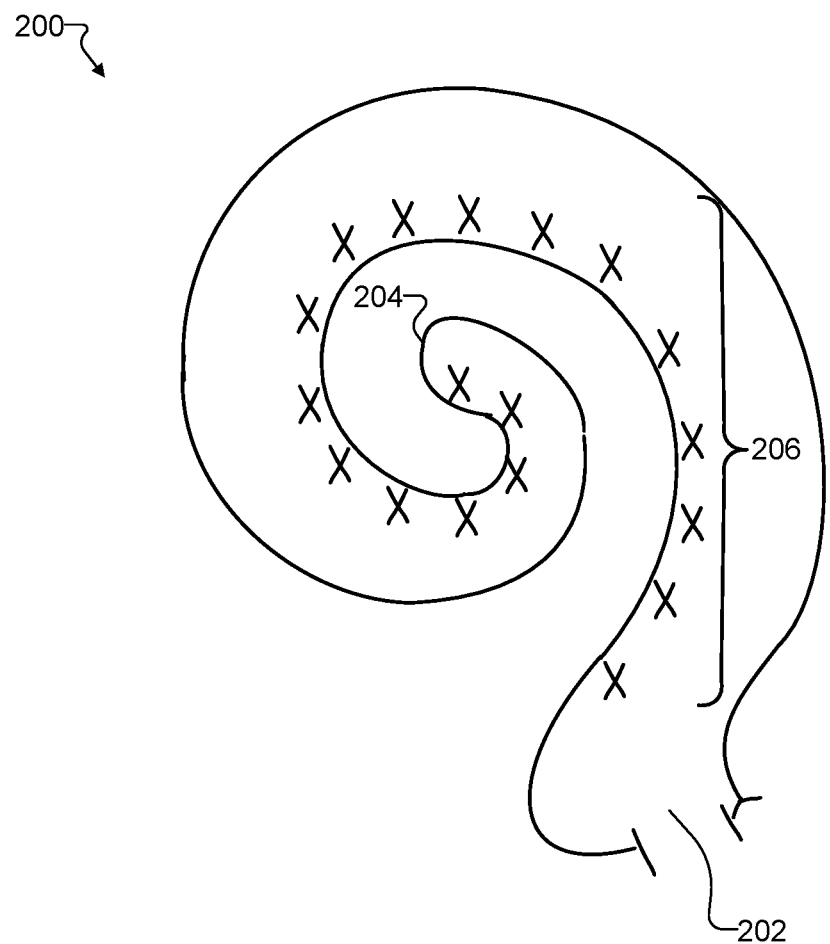
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the electrode lead, the anatomy of the patient's cochlea, and/or any other factor as may serve a particular implementation.

Figure 3:
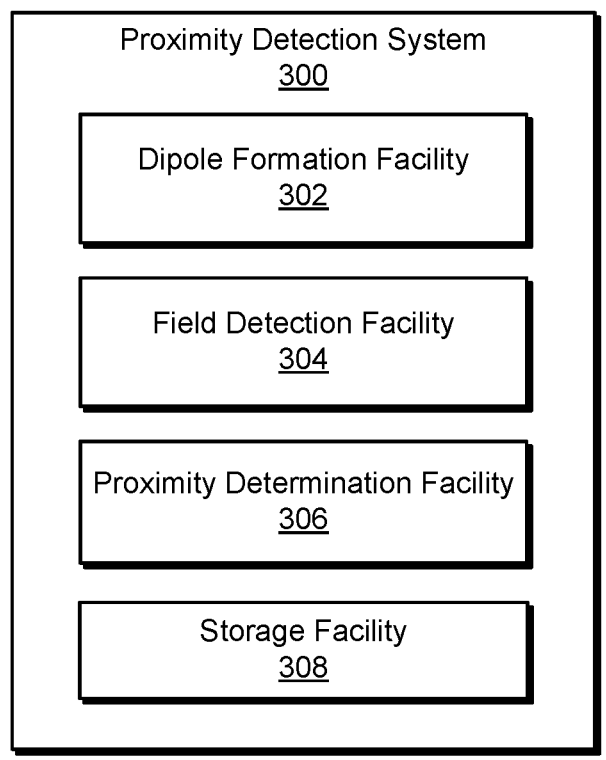
FIG. 3 illustrates an exemplary proximity detection system for detecting electrode lead proximity to cochlear tissue according to principles described herein.

FIG. 3 illustrates an exemplary proximity detection system 300 ("system 300") for detecting electrode lead proximity to cochlear tissue in accordance with principles described herein. As shown, system 300 may include a dipole formation facility 302, a field detection facility 304, a proximity determination facility 306, and a storage facility 308, which may be selectively and communicatively coupled to one another. It will be recognized that although facilities 302 through 308 are shown to be separate facilities in FIG. 3, facilities 302 through 308 may be combined into fewer facilities, such as into a single facility, or divided into more facilities as may serve a particular implementation. In some examples, system 300 may include, implement, or be implemented by a sound processor within a cochlear implant system (e.g., sound processor 104), by a cochlear implant system itself (e.g., cochlear implant system 100), by an external computing device separate from and communicatively coupled to a cochlear implant system, by any combination thereof, and/or by any other suitable system or device as may serve a particular implementation. Each of facilities 302 through 308 will now be described in more detail.

Dipole formation facility 302 may be configured to form a dipole by directing equal and opposite pulses to be generated on an electrode lead that is electrically coupled to a cochlear implant and is configured to be inserted into a cochlea of a patient. Specifically, for example, dipole formation facility 302 may direct the cochlear implant to apply a first pulse by way of a first electrode disposed on the electrode lead, and to apply, concurrently with the application of the first pulse, a second pulse by way of a second electrode disposed on the electrode lead. The second pulse may have a substantially equal magnitude and an opposite phase to the first pulse such that the application of the first and second pulses forms a dipole that generates a field. Exemplary types of dipoles and fields that may be generated by dipole formation facility 302 will be described in more detail below Dipole formation facility 302 may include or be implemented by one or more physical computing devices (e.g., including hardware and/or software such as processors, memories, communication interfaces, instructions stored in memory for execution by the processors, etc.) included in a sound processor of a cochlear implant system (e.g., sound processor 104). In some examples, dipole formation facility 302 may further include the cochlear implant and a current source included therein that is directed to apply the pulses, as well as the electrode lead by way of which the pulses are applied. In other examples, these elements may be separate from and communicatively coupled to dipole formation facility 302. Additionally, in certain examples, computing devices external to the cochlear implant system may implement or be included within dipole formation facility 302. For instance, such external computing devices may be used to control the sound processor as the sound processor directs the cochlear implant to perform the dipole formation operations described above.

Field detection facility 304 may direct the cochlear implant to detect an energy magnitude of the field generated by the dipole formed by dipole formation facility 302 as the field reflects from cochlear tissue located within the field. For example, field detection facility 304 may direct the cochlear implant to detect the energy magnitude by way of a third electrode disposed on the electrode lead. Exemplary types of fields and field energies for which a magnitude may be detected will be described in more detail below.

Proximity determination facility 306 may determine (e.g., calculate, compute, etc.) a proximity of the electrode lead to the cochlear tissue. For example, proximity determination facility 306 may determine the proximity based on a difference between the energy magnitude of the field detected by field detection facility 304 and a baseline energy magnitude of the field (e.g., a baseline accessed from storage facility 308, determined by proximity determination facility 306 or another facility within system 300, etc.). Exemplary types of detected and baseline energy magnitudes that may be analyzed by proximity determination facility 306 in making the proximity determination will be described in more detail below.

As described above with respect to dipole formation facility 302, field detection facility 304 and proximity determination facility 306 may each include or be implemented by one or more physical computing devices (e.g., the same computing devices and/or different computing devices as described above for dipole formation facility 302). As further described above with respect to dipole formation facility 302, facilities 304 and 306 may each additionally include certain elements of the cochlear implant system (e.g., a voltage detector included within the cochlear implant for detecting the energy magnitude of the field) and/or of one or more external computing devices communicatively coupled to the cochlear implant system in certain implementations. In other implementations, facilities 304 and 306 may be implemented exclusively by computing components within the sound processor.

In some examples, facilities 302 through 306 may perform the operations described above in real time during an insertion procedure (e.g., while the surgical insertion procedure is ongoing). As used herein, an operation is considered to be performed in "real time" when the operation is performed immediately and without undue delay (e.g., in real time or near real time). Accordingly, operations may be said to be performed in real time and users of system 300 may be considered to receive real time information during the insertion procedure even if the information is provided after a small delay (e.g., up to a few seconds).

Storage facility 308 may maintain any data received, generated, managed, maintained, used, and/or transmitted by facilities 302 through 306 in a particular implementation. For example, storage facility 308 may store data representative of pulse magnitudes and/or phases configured to generate the dipoles, data representative of energy magnitudes detected from the field reflecting from the cochlear tissue, data representative of baseline energy magnitudes used to compare to the detected energy magnitudes in the determination of the proximity, or the like. Storage facility 308 may further include any other data as may serve a particular implementation of system 300 to facilitate performing one or more of the operations described herein.

To illustrate system 300 in operation detecting electrode lead proximity to cochlear tissue, FIGS. 4A through 4C depict exemplary aspects of detecting an electrode lead proximity to cochlear tissue during an exemplary insertion procedure. Specifically, as shown in FIGS. 4A, 4B, and 4C, respectively, different snapshots 400-1, 400-2, and 400-3 of a cutaway view of cochlea 200 are illustrated representing three different moments during an insertion procedure in which an electrode lead 402 is being inserted into cochlear 200. Specifically, snapshot 400-1 corresponds to a moment relatively early in the insertion procedure, snapshot 400-2 corresponds to a moment later in the insertion procedure, and snapshot 400-3 corresponds to a moment even later in the insertion procedure.

In snapshot 400-1 in FIG. 4A, electrode lead 402 is depicted to be emitting a field 404-1 around a distal tip of electrode lead 402. For example, field 404-1 may be an electric field generated by an electric dipole formed by an application of equal and opposite current pulses by way of two nearby (e.g., adjacent) electrodes near the distal tip of electrode lead 402. In other examples, field 404-1 may be another type of field generated by another type of dipole, as will be described in more detail below. While fields generated by dipoles formed by electrode lead 402 and/or other electrode leads described herein may theoretically extend out into space in an unbounded manner, for practical purposes, such fields may be configured to have a significant energy magnitude (e.g., a detectable energy magnitude) only within a relatively small volume immediately surrounding the dipoles generating the fields. For example, a field generated by a dipole formed by electrodes on electrode lead 402 may have a significant energy magnitude only within a volume bounded by a sphere representing field 404-1 in FIG. 4A (drawn as a two-dimensional circle in the cutaway view of FIG. 4A). Such a volume may be referred to herein as the "local volume" around the dipole, and it will be understood that, as used herein, field 404-1 (and other fields described herein) may refer only to the portion of the field contained within the local volume around the dipole, rather than the entire unbounded field.

As shown in snapshot 400-1, field 404-1 (i.e., the portion of the field extending from the dipole formed by electrode lead 402 that is in the local volume around the dipole) may not interact with any cochlear tissue of cochlea 200 at the point in time near the beginning of the insertion procedure represented by snapshot 400-1. Specifically, field 404-1 is contained within cochlear fluids and the like that may be present in cochlea 200, but may not be near enough to any tissue (e.g., wall) of cochlea 200 to be detectably altered by interaction with the tissue. In some examples, it may be known that an energy magnitude of field 404-1 is substantially unaffected by cochlear tissue soon after electrode lead is inserted into the base of cochlea 200, as shown in snapshot 400-1. Accordingly, the energy magnitude of field 404-1 detected at this point in the insertion procedure may be detected and stored for use as a baseline energy magnitude to be compared with other energy magnitudes of similar fields generated later in the insertion procedure.

For example, an energy magnitude of field 404-1 may be used as a baseline energy magnitude to compare with a detected energy magnitude of a field 404-2 generated at a later point in the insertion procedure, as depicted in snapshot 400-2 of FIG. 4B. Field 404-2 may be generated in the same manner as field 404-1 (i.e., by an equivalent dipole formed by the same electrodes applying the same magnitudes and phases of pulses). However, because of the depth at which electrode lead 402 is positioned in snapshot 400-2 at the later moment in the insertion procedure, field 404-2 is depicted to overlap with cochlear tissue of cochlea 200. Specifically, as shown, field 404-2 intersects cochlear tissue within a volume 406-1. Volume 406-1 of the cochlear tissue may alter the energy magnitude of field 404-2 that will be detected by electrodes on electrode lead 402. For example, as will be described in more detail below, the close proximity of volume 406-1 to the dipole generating field 404-2 may result in an increased amount of energy of field 404-2 reflecting back to electrodes detecting the energy magnitude, such that the electrodes detect an increased energy magnitude as compared to a baseline energy magnitude (e.g., a baseline energy magnitude associated with field 404-1, as described above). As another example, the close proximity of volume 406-1 to the dipole generating field 404-2 may result in an absorption of some of the energy of field 404-2 that might otherwise have been reflected back, such that the electrodes detect a decreased energy magnitude as compared to the baseline energy magnitude. Accordingly, the energy magnitude of field 404-2 that is detected during snapshot 400-2 may indicate that electrode lead 402 is in close proximity to cochlear tissue of cochlea 200 and, in some implementations, how proximate the cochlear tissue is to electrode lead 402.

Snapshot 400-3 illustrates yet another field 404-3 that may be generated in the same manner as fields 404-1 and 404-2. At the depth of electrode lead 402 in snapshot 400-3, field 404-3 may again be detected to be in close proximity to cochlear tissue of cochlea 200. For example, a volume 406-2 of cochlear tissue may detectably alter the energy magnitude of field 404-3 in any of the ways described above for volume 406-1 and field 404-2.

Further illustrated in FIG. 4C, a field 404-4 may be generated to detect proximity of electrode lead 402 with volume 406-1 of the cochlear tissue. While fields 404-2 and 404-3 may be generated by a dipole formed near the distal tip of electrode lead 402, field 404-4 is generated by a dipole formed at a more proximal portion of electrode lead 402, as shown. This may be helpful to determine the proximity of electrode lead 402 to the cochlear tissue along the entire length of the inserted portion of the electrode lead, rather than just at the leading tip. As will be described in more detail below, different types of tissue at different parts of cochlea 200 may reflect fields 404 in different manners that may not only indicate the proximity of the tissue to electrode lead 402, but may also indicate certain characteristics of the tissue (e.g., how soft or bony the tissue is, what type of tissue is present, etc.).

As mentioned above, in some examples, system 300 may perform operations such as directing the cochlear implant to apply the first and second pulses (i.e., to form the dipole that generates the field), directing the cochlear implant to detect the energy magnitude of the field, and determining the proximity of electrode lead 402 to the cochlear tissue of cochlea 200 during an insertion procedure in which electrode lead 402 is being surgically inserted into cochlea 200. As such, in these examples, system 300 may further provide, during the insertion procedure and based on the determined proximity of electrode lead 402 to the cochlear tissue, real-time feedback configured to facilitate the insertion procedure. For example, the real-time feedback may include a notification or warning (e.g., a sound, a flashing light, a warning message, etc.) indicating that electrode lead 402 is in close proximity to the cochlear tissue and/or how proximate electrode lead 402 is to the cochlear tissue. Additionally, in certain examples, the real-time feedback may include information that has been determined about the characteristics of the tissue (e.g., based on the types of reflections that have been detected, as mentioned above and as will be described in more detail below).

In some examples, system 300 may provide such real-time feedback by way of another device. For example, if system 300 is implemented by a sound processor communicatively coupled with an external computing device, system 300 may provide the real-time feedback by directing the external computing device to present the real-time feedback to a user by way of a display screen, loudspeaker, or other output component associated with the external computing device. Additionally, in some implementations, the real-time feedback may be presented in the form of haptic feedback (e.g., a vibration applied to instruments the surgeon is using, etc.).

Providing real-time feedback during an insertion procedure may facilitate the insertion procedure in a variety of ways. For example, in situations where a steerable electrode lead is being used, a surgeon performing the insertion procedure may use the real-time feedback to determine how and when to steer the electrode lead. In like manner, such feedback may be employed in robotically-assisted insertion procedures in which a computer receiving the real-time feedback directs a robotic mechanism to steer and advance the electrode lead in accordance with the feedback in a similar fashion. Moreover, the real-time feedback may facilitate an insertion procedure by indicating (e.g., to a surgeon, to a computer directing a robotic mechanism, etc.) that an angle of insertion is to be adjusted, that ultrasonic vibrations are to be applied (e.g., to help prevent the electrode lead from becoming stuck and translocating or otherwise causing tissue trauma), that an insertion point (e.g., in the round window of the cochlea) is to be extended or opened wider, that the electrode lead is to be rotated, that the insertion procedure is complete and a stylet or insertion tube is now to be removed, and/or any other such information as may serve a particular implementation.

In other examples, system 300 may detect electrode lead proximity to cochlear tissue at times other than when an insertion procedure is ongoing. For example, system 300 may perform the directing of the cochlear implant to apply the first and second pulses, the directing of the cochlear implant to detect the energy magnitude, and the determining of the proximity of electrode lead 402 to the cochlear tissue of cochlea 200 subsequent to the insertion procedure. In other words, system 300 may perform these operations at a point in time subsequent to snapshots 400-1 through 400-3 when electrode lead 402 has been completely inserted and is at rest at a position within cochlea 200. In these examples, it may be less important to receive real-time feedback indicative of the proximity of electrode lead 402. However, system 300 may still provide data indicative of the position within cochlea 200 at which electrode lead 402 rests (e.g., including data related to all of the electrodes and not only the most distal ones). This data may be provided and presented directly by system 300 and/or by way of another device in any of the ways described herein.

Providing data indicative of the position within cochlea 200 at which electrode lead 402 rests may provide certain similar benefits as those described above in relation to the real-time feedback provided during the insertion procedure, as well as additional benefits such as for fitting the cochlear implant based on information about whether the electrode is in proximity to the tissue or not. For instance, as illustrated by field 404-4 in FIG. 4C, electrodes other than the distal-most electrode on the electrode lead may be used to determine the proximity of more proximal portions of electrode lead 402 (i.e., portions other than the distal tip with which fields 404-1 and 404-2 are associated). In other words, in some examples, an electrode other than the first, second, or third electrodes used to form the dipole and detect the energy magnitude may be disposed on the electrode lead at the distal-most electrode position on the electrode lead.

By determining the proximity of not only the distal tip of electrode lead 402 but also other more proximal portions, it may be determined (e.g., during a fitting process of the newly implanted cochlear implant to the patient) that certain channels may be focused, amplified, disabled, combined, or the like. For example, if the resting position of electrode lead 402 within cochlear 200 is such that an electrode implementing one channel substantially overlaps with another electrode implementing another channel, it may be determined that the channels are substantially redundant and one of them may be disabled or otherwise adjusted as may be appropriate.

Data indicative of the resting position of the electrode leads may also be valuable for research purposes. For example, researchers may help improve future insertion procedures and hearing outcomes for patients by studying outcomes of patients with electrode leads having different final resting positions (e.g., having different depths, different electrodes making physical contact with the modiolus, etc.). As another example, researchers may be able to better study and understand new technologies such as electrode leads constructed using shape memory material or the like when the resting position of the electrode leads can be conveniently determined directly after an insertion procedure as well as at various additional times in the future.

In some examples, determining electrode lead proximity to cochlear tissue subsequent to the insertion procedure may further allow fitting parameters to be appropriately adjusted.

For example, if a patient gets ill and runs a fever that increases the temperature within the cochlea, the resting position of the electrode lead may temporarily change until the fever subsides. As such, it may be desirable for the cochlear implant system to detect the change and automatically adjust fitting parameters appropriately such that the patient may not notice a difference in his or her hearing while the fever persists.

To illustrate how electrode lead 402 may operate to perform the functionality and provide the benefits described in relation to FIGS. 4A through 4C, FIG. 5A illustrates an exemplary implementation of electrode lead 402 within an exemplary cochlear implant system (e.g., cochlear implant system 100). Specifically, FIG. 5A depicts electrode lead 402 as being part of a cochlear implant system that further includes a sound processor 502 external to the patient's skin and a cochlear implant 504 implanted within the patient and physically coupled to electrode lead 402. Sound processor 502 may perform similar operations as described above with respect to sound processor 104 of cochlear implant system 100. Additionally, sound processor 502 may be configured to implement system 300 and, as such, may direct cochlear implant 504 to perform any of the operations described herein with respect to electrode lead 402.

As labeled in FIG. 5A, electrode lead 402 may include a proximal portion near the coupling with cochlear implant 504 and a distal portion configured for insertion into a cochlea of a patient (e.g., cochlea 200). Disposed on the distal portion of electrode lead 402 is a plurality of electrodes 506 (e.g., electrodes 506-1 through 506-4 and 506-16, which are explicitly labeled, and additional electrodes 506-5 through 506-15, which are not explicitly labeled in FIG. 5A but may be referred to herein). Electrodes 506 may be configured to be disposed within the cochlea to apply stimulation to the patient when the insertion procedure is complete and electrode lead 402 is located at its resting position. As such, electrodes 506 may be referred to as "stimulating electrodes."

Further illustrated in FIG. 5A on the distal portion of electrode lead 402 (i.e., at the distal tip of electrode lead 402) is an electrode 508. Electrode 508 may not be configured to (or at least may not typically be used to) apply stimulation to the patient to cause hearing perception (e.g., during regular daily operation). Rather, as will be described in more detail below, electrode 508 may be used by system 300 to detect the energy magnitude of a field generated by a dipole formed by pulses applied by two or more of electrodes 506. Accordingly, electrode 508 may be referred to herein as a "sensing electrode," and electrodes 506 and 508 may collectively be referred to herein as "distal electrodes."

On the proximal portion of electrode lead 402, an additional electrode 510 is also depicted. Electrode 510 may be configured to be a ground electrode and, as such, may remain outside the cochlea even after the insertion procedure is complete. As shown, electrode 510 may be implemented as a ring electrode that goes all the way around the circumference of electrode lead 402. Electrode 510 and/or other similar ground electrodes referred to herein may be referred to herein as "proximal electrodes" to distinguish them from distal electrodes 506 and 508.

In FIG. 5A, various aspects of electrode lead 402 are simplified for clarity of illustration. For instance, while electrode lead 402 is illustrated in a straightened configuration in FIG. 5A, it will be understood that, as illustrated in by electrode lead 110 in FIG. 1, electrode lead 402 may be configured to follow the curved, spiral-shaped structure of cochlea 200. Additionally, it will be understood that the length and width of electrode lead 402, the size and relative spacing of the electrodes included on electrode lead, and various other aspects of the components depicted in FIG. 5A and other figures included herein may not be drawn to scale.

In operation, electrode lead 402 may use two electrodes (e.g., two of stimulating electrodes 506) to form a dipole. For example, under direction from sound processor 502, cochlear implant 504 may cause a first pulse to be applied at a first electrode 506 (e.g., electrode 506-1) and a second pulse to be applied at a second electrode 506 (e.g., electrode 506-2). The first and second pulses may be applied concurrently and so as to have substantially equal magnitude and opposite phase. As such, and because the electrodes at which the pulses are applied are in close proximity to one another, the application of the first and second pulses may form a dipole. For example, if the pulses applied are current pulses generated by a current source included within cochlear implant 504, the dipole formed may be an electric dipole that generates an electric field.

In other examples, other types of pulses may be applied so as to form other types of dipoles that generate other types of fields. For example, optical pulses (e.g., carried by optical fibers in electrode lead 402 that are not explicitly shown) may be applied to form an optical dipole generating an optical field, magnetic pulses may be applied to form a magnetic dipole generating a magnetic field, or the like.

Concurrently with, or immediately subsequent to, the formation of the dipole by the application of the pulses, one or more electrodes on electrode lead 402 may be used to detect an energy magnitude of the field generated by the dipole (e.g., as the field reflects from cochlear tissue that may be proximate to electrode lead 402). Based on the detected energy magnitude of the field, as described above, system 300 may determine a proximity of electrode lead 402 to cochlear tissue surrounding it (e.g., volumes 406-1 and 406-2 of the cochlear tissue of cochlea 200 illustrated in FIGS. 4B and 4C). As used herein, a proximity "of an electrode lead" may refer to the electrode lead as a whole, to any particular electrode or consecutive subset of electrodes on the electrode lead, a particular part of the electrode lead (e.g., a distal tip of the electrode lead where an electrode such as electrode 508 may or may not be disposed), or the like.

For instance, in an example in which electrodes 506-1 and 506-2 are used as the first and second electrodes by way of which the first and second pulses are applied to form the dipole and in which electrode 508 is used as the third electrode by way of which the energy magnitude of the field is detected, the proximity of electrode lead 402 to the cochlear tissue may refer to the proximity of one or more of electrodes 506-1, 506-2 and 508 to the cochlear tissue. Conversely, in other examples in which other electrodes are employed, the proximity of electrode lead 402 may refer to the proximity of the other electrodes to the cochlear tissue. Additionally, in certain examples in which no sensing electrode equivalent to electrode 508 is present at the distal tip of an electrode lead, the computation of the proximity may account for the extra material of the electrode lead between the distal-most electrode and the actual distal tip of the electrode lead so that the proximity of the electrode lead may refer specifically to the proximity of the distal tip of the electrode lead.

The first and second electrodes at which the pulses are applied to form the dipole, as well as the third electrode at which the energy magnitude of the field is detected, may be implemented by any of the electrodes on electrode lead 402 in any suitable configuration. For example, the first and second electrodes may be disposed at adjacent electrode positions on electrode lead 402 (e.g., so as to be less than 1 mm apart in certain examples). A theoretically ideal dipole would include equal and opposite charges at the same point in space. Thus, while this is not possible or practical to implement in a real (i.e., non-theoretical) application, system 300 may form the best dipole possible by directing cochlear implant 504 to apply the pulses at electrodes that are close by one another (e.g., less than 1 mm apart in certain implementations). In this way, the field will be highly focused and system 300 may achieve accurate results. In some implementations, it may also be possible to employ non-adjacent electrodes to form the dipole if the non-adjacent electrodes are sufficiently close by one another.

In certain configurations (e.g., configurations in which electrode lead 402 does not include a sensing electrode such as electrode 508), stimulating electrodes 506 may be used exclusively to form the dipole and detect the energy magnitude of the field generated by the dipole. For example, the third electrode may be disposed on electrode lead 402 at a distal-most electrode position on electrode lead 402 (i.e., may be implemented by electrode 506-1), and the first and second electrodes may be disposed on electrode lead 402 at respective electrode positions more distal than any other electrode positions besides the distal-most electrode position of the third electrode (i.e., may be implemented by electrodes 506-2 and 506-3). As mentioned above, in other examples, other more proximal electrodes may be employed (e.g., to detect the resting position of electrode 402 subsequent to the completion of the insertion procedure). For example, the first and second electrodes may be implemented by electrodes 506-14 and 506-15, while the third electrode may be implemented by electrode 506-16. Accordingly, in these examples, electrode 506-1 disposed on electrode lead 402 at the distal-most electrode position does not implement the first, second, or third electrodes.

In other configurations, stimulating electrodes 506 may be used to form the dipole, while sensing electrode 508 may be used to detect the energy magnitude of the field. In other words, the third electrode may be implemented by electrode 508 disposed right at the distal-most tip of electrode lead 402. As mentioned above, electrode 508 may be implemented as a sensing electrode that is configured to detect the energy magnitude of the field and is not configured to apply stimulation to the patient.

FIG. 5B illustrates an alternative view of the most distal portion of electrode lead 402. Specifically, FIG. 5B illustrates a view from below the portion of electrode lead 402 as depicted in FIG. 5A. As illustrated, electrodes 506 may be implemented as half-ring electrodes that extend in a semicircle halfway around the circumference of electrode lead 402. Such a configuration may allow stimulating electrodes to efficiently apply stimulation to cochlear tissue directly where the electrodes contact the tissue. Conversely, sensing electrode 508 may be implemented using a different design, as shown. Specifically, electrode 508 may include a plurality of thin conductors (e.g., conductors 508-1 through 508-5) distributed around the distal tip of electrode lead 402 to provide a high degree of sensitivity in sensing the energy magnitude of the field. For example, conductors 508 may be constructed from platinum wires or another material as may serve a particular implementation.

Returning to FIG. 5A, cochlear implant 504 is depicted as being enclosed within a hermetically sealed housing 512. Housing 512 is shown to be associated with a case ground 514 (i.e., a ground contact electrically coupled to housing 512) and to include a feedthrough assembly 516 whereby electrode lead 402 is electrically coupled to internal components of cochlear implant 504 sealed inside of housing 512. Like ground electrode 510, case ground 514 may be used as a ground contact for certain measurements performed by cochlear implant 504 as will be described in more detail below.

Feedthrough assembly 516 may be configured to provide an electrical pathway between internal circuitry of cochlear implant 504 and conductors external to cochlear implant 504 (e.g., case ground 514 and/or electrodes 506, 508, and/or 510) while maintaining the hermetic seal separating the internal circuitry from the tissue of the patient within which cochlear implant 504 may be implanted. In certain examples, feedthrough assembly 516 may be configured with a limited number of feedthrough conductors. For example, for conventional electrode lead configurations, a feedthrough assembly may be configured to provide eighteen conductors to accommodate sixteen stimulating electrodes, one ground electrode, and one case ground contact. When such feedthrough assemblies are employed, there may not be a dedicated feedthrough conductor available to accommodate a sensing electrode such as electrode 508 that may be included to facilitate detecting electrode lead proximity to cochlear tissue. However, because the sensing electrode may only be configured to implement the third electrode (i.e., the electrode that detects the energy magnitude of the field) and not to apply stimulation to the patient, the sensing electrode may be electrically coupled to the cochlear implant by way of a common feedthrough conductor also used to electrically couple another electrode to the cochlear implant (e.g., another electrode that is configured to apply stimulation to the patient). For example, sensing electrode 508 may be electrically coupled to cochlear implant 504 by way of a common feedthrough conductor within feedthrough assembly 516 that is also used to electrically couple a stimulating electrode 506 such as stimulating electrode 506-16 to cochlear implant 504.

In order to generate the pulses applied by way of the first and second electrodes of electrode lead 402 and to detect the energy magnitude of the field by way of the third electrode as described above, cochlear implant 504 may include pulse generation and detection circuitry. For example, such circuitry may be enclosed within housing 512 and may be configured to control electrodes on electrode lead 402 based on direction received from sound processor 502.

Figure 6A:
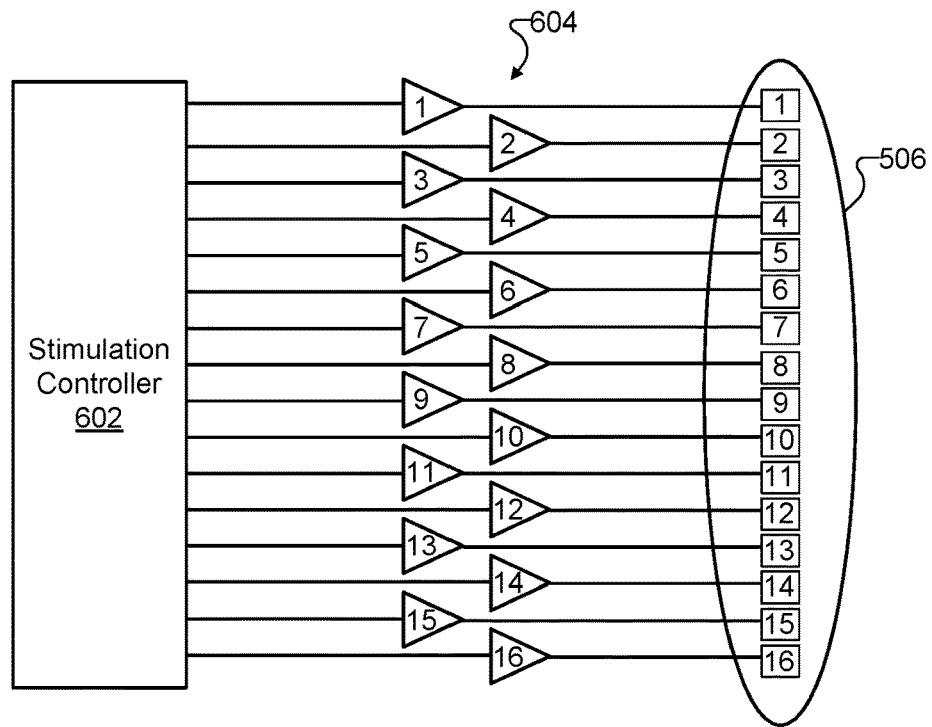
FIG. 6A illustrates exemplary circuitry for applying pulses by way of stimulating electrodes included on an electrode lead according to principles described herein.
Figure 6B:
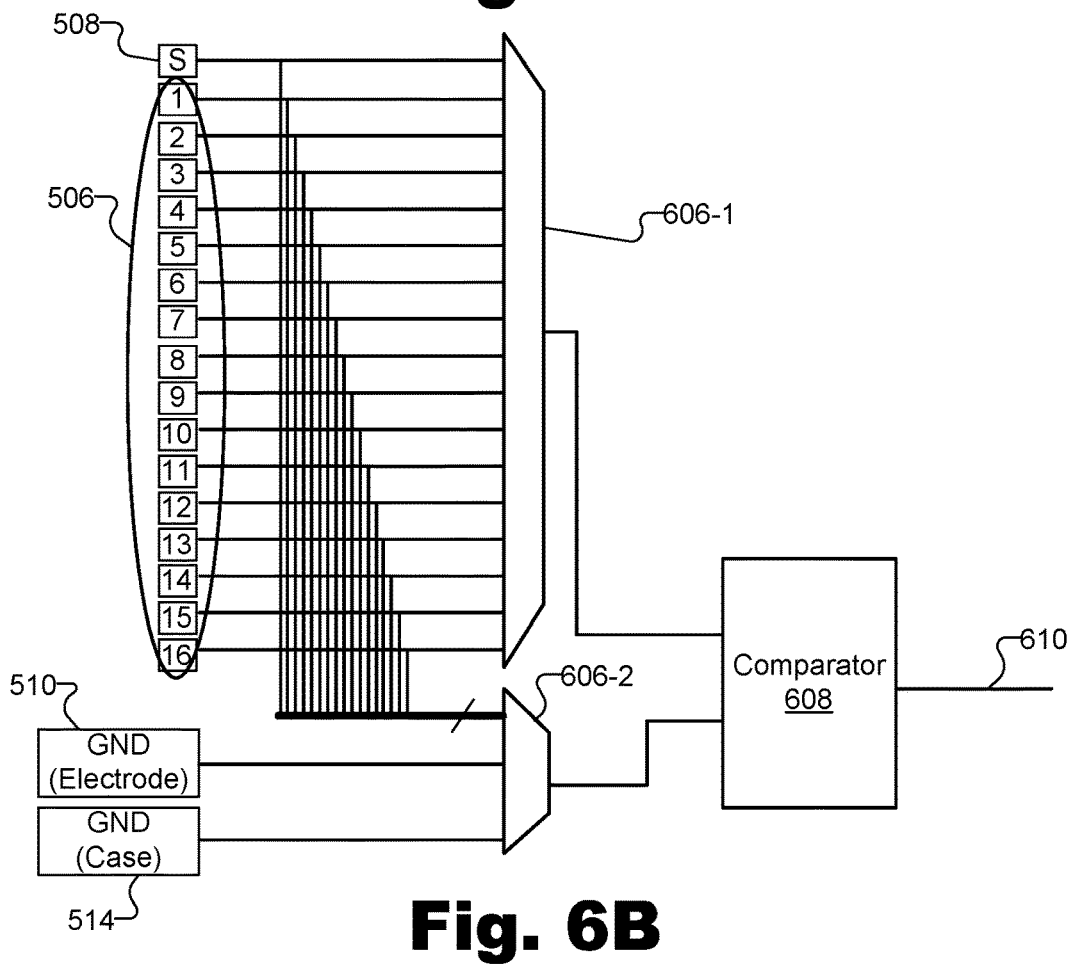
FIG. 6B illustrates exemplary circuitry for detecting an energy magnitude of a field generated by a dipole by way of an electrode included on an electrode lead according to principles described herein.

To illustrate an example of such circuitry, FIG. 6A shows exemplary circuitry for applying pulses by way of stimulating electrodes 506, while FIG. 6B shows exemplary circuitry for detecting an energy magnitude of a field generated by a dipole by way of an electrode 506 or 508.

Specifically, FIG. 6A shows a stimulation controller 602 included within cochlear implant 504. Stimulation controller 602 may be configured to direct electrodes 506 to apply electrical stimulation to the patient during normal operation, as described above. Additionally, stimulation controller 602 may be integrated into and/or controlled by system 300 and, as such, may be further configured to periodically direct pulses (e.g., non-stimulation pulses that are not perceivable by the patient) to be applied so as to form a dipole. Specifically, as described above, the pulses may have substantially equal magnitude and opposite phase (i.e., one having a positive value and the other having a negative value) and may be applied concurrently by way of two electrodes 506.

As shown, each electrode 506 may be associated with a particular driver 604 (i.e., one of drivers 604-1 through 604-16, labeled "1" through "16" under the "604" callout in FIG. 6A) configured to generate a pulse at the electrode 506 when directed by stimulation controller 602. For example, each driver 604 may be implemented by a current source, a voltage source, or the like. As such, stimulation controller 602 may include logic for receiving direction from dipole formation facility 302 of system 300 and, in response to the received direction, may direct at least one of drivers 604 to generate a pulse (e.g., an electrical pulse such as a current pulse or a voltage pulse) at the respective electrodes 506. For instance, if dipole formation facility 302 directs stimulation controller 602 to concurrently apply pulses at electrodes 506-1 and 506-2, stimulation controller 602 may cause drivers 604-1 and 604-2 to concurrently generate equal and opposite electrical pulses to be applied by way of these electrodes.

In some examples, the pulses generated by drivers 604 for detecting electrode lead proximity to cochlear tissue may be pulses that are perceived to a lesser extent or not at all by users (in contrast to normal stimulation pulses generated by drivers 604 during normal operation of the cochlear implant system). For example, the pulses for detecting electrode lead proximity to cochlear tissue may be sub-threshold pulses (i.e., pulses applied at a lower magnitude than the patient can perceive). As another example, the pulses may be at a magnitude level that is above the threshold that the patient can perceive, but may still be unperceivable due to an equal and opposite pulse concurrently being generated. In other words, for instance, because one electrode may be sourcing a certain amount of current at the same time that a nearby electrode is sinking the same amount of current, the current may not stimulate the cochlear tissue in a perceivable way.

Once a dipole has been formed by equal and opposite pulses applied at two electrodes 506, FIG. 6B illustrates how the magnitude (e.g., strength, etc.) of the energy of the field generated by the dipole may be detected in certain exemplary implementations. Just as stimulation controller 602 may be configured to generate pulses at arbitrary electrodes 506 as described above, the detection circuitry illustrated in FIG. 6B may provide similar flexibility in detecting energy magnitudes of a field by way of any electrode 506 or 508 with respect to one another or with respect to ground electrode 510 or case ground 514. For example, the energy magnitude of a field may be detected by detecting a voltage differential between two distal electrodes (i.e., two of electrodes 506 and/or 508), between one distal electrode and ground electrode 510, or between one distal electrode and case ground 514. To this end, as shown, the circuitry of FIG. 6B includes multiplexors 606 (e.g., multiplexors 606-1 and 606-2), which are configured to switch any of the distal electrodes into a first terminal of a comparator 608, and to switch any of the distal electrodes 506 or 508, ground electrode 510, or case ground 514 into a second terminal of comparator 608.

It will be understood that additional inputs may also be included in multiplexors 606 in certain implementations that are not shown in FIG. 6B. For example, all of the electrodes and grounds illustrated in FIG. 6B, as well as additional contacts, may be available as inputs to one or both of multiplexors 606 in certain implementations to provide for maximum flexibility. Multiplexors 606 may be under control of system 300 (e.g., field detection facility 304 in particular) such that appropriate bipolar measurements (i.e., between two distal electrodes) and/or monopolar measurements (i.e., between a distal electrode and a ground electrode or other ground contact) may be taken as directed by system 300. For example, system 300 may direct cochlear implant 504 to detect the energy magnitude of the field by directing multiplexors 606 to select, for comparison by comparator 608, one of electrodes 506 and 508 and a ground reference that is electrically distinct from any electrode that is disposed on the distal portion of electrode lead 402 (e.g., ground electrode 510 or case ground 514). As another example, system 300 may direct cochlear implant 504 to detect the energy magnitude of the field by directing multiplexors 606 to select, for comparison by comparator 608, two distal electrodes (e.g., electrode 508 and one of electrodes 506 such as electrode 506-3 if electrodes 506-1 and 506-2 are being used to apply the pulses forming the dipole).

Comparator 608 may be implemented as voltage detector or other similar circuit for comparing signals selected by multiplexors 606. For example, comparator 608 may include a differential amplifier that generates a signal 610 representative of an energy magnitude of a field. For instance, signal 610 may be a voltage signal indicative of a voltage difference measured between the electrodes selected, by multiplexors 606, for comparison by comparator 608. Signal 610 may then be used by system 300 (e.g., proximity determination facility 306 in particular) to determine the proximity of electrode lead 402 to the cochlear tissue (e.g., based on a difference between signal 610 and a signal representative of a baseline energy magnitude of the field).

In certain conventional systems, impedance measurements may be performed for various reasons including, in some examples, to determine information related to an insertion depth of an electrode lead within a cochlea. For example, an impedance measurement may be performed by applying a current pulse by way of a particular stimulating electrode and detecting a voltage by way of the same stimulating electrode (e.g., a voltage with respect to a ground electrode). Based on a known level of the current applied and based on the measured voltage level, an impedance may be determined based on Ohm's law or a variant thereof. Additionally, in some examples, a cross-impedance measurement may be performed by applying the stimulation current at one electrode and detecting the voltage at a different electrode. Such cross-impedance measurements may help determine, for instance, which electrodes may have entered into the cochlea and which ones are still outside the cochlea, whether a tip fold-over has occurred (e.g., if electrodes are determined to be folded), or the like, thus providing the surgeon with information related to the progress and status of the insertion procedure.

In some implementations, the systems and methods for detecting electrode lead proximity to cochlear tissue described herein may employ impedance measurements that have certain characteristics in common with the conventional impedance measurements described above. For example, equal and opposite pulses applied by way of the first and second electrodes to form the dipole may be current pulses of a predetermined current level, and the energy magnitude of the field may be detected by way of the third electrode by detecting a voltage at the third electrode and using Ohm's law to convert the detected voltage into a detected impedance representative of the energy magnitude. However, it will be understood that such impedance measurements performed by proximity detection systems and methods described herein may be differentiated from conventional impedance measurements described in many ways. For example, as described above, current pulses applied by these systems are applied in concurrent, equal-and-opposite pairs by way of two different electrodes, rather than applying a single pulse on a single electrode. As such, dipoles may be formed that generate fields that are detectable to a proximity detection system, while no stimulation perceivable by the patient may be actually presented. Additionally, it will be understood that while a monopolar measurement similar to conventional impedance measurements described above may be employed in certain implementations of the proximity detection systems and methods described herein, other implementations may employ bipolar measurements whereby two additional distal electrodes (i.e., electrodes separate from the two electrodes by way of which the pulses are applied) are used to detect the voltage.

To illustrate, FIG. 7A shows exemplary pulses that are applied concurrently at first and second electrodes to have substantially equal magnitudes and opposite phases (i.e., opposite signs), while FIG. 7B shows exemplary detected pulses representative of energy magnitudes of fields generated by dipoles formed by the application of the pulses of FIG. 7A. Each graph shown in FIGS. 7A and 7B illustrates pulses being applied or detected with respect to time, which is represented along each respective x-axis. Along the y-axis, the graphs illustrated in FIG. 7A depict, for both a first electrode ("Electrode 1") and a second electrode ("Electrode 2"), a current level of a sequence of concurrently-applied current pulses having equal and opposite magnitude. Along the y-axis of FIG. 7B, a detected voltage level is depicted.

Referring to FIG. 7A, the graphs for Electrode 1 and Electrode 2 depict a series of concurrent pulses 702 including a particular concurrent pulse 704 consisting of equal and opposite biphasic pulses 704-1 (applied by way of Electrode 1) and 704-2 (applied by way of Electrode 2). In other words, as shown, when pulse 704-1 has a current level at a particular magnitude above zero (i.e., so as to be sourcing current) pulse 702-2 has a current level at the particular magnitude below zero (i.e., so as to be sinking current).

As shown, concurrent pulses 702 (including concurrent pulse 704) may be implemented by biphasic current pulses. That is, each pulse applied by a particular electrode may include both a positive magnitude phase and a negative magnitude phase. For example, as shown, concurrent pulse 704 includes a first phase of duration 706-1 in which a first positive magnitude of current is applied at Electrode 1 (as part of biphasic pulse 704-1) concurrently with a first negative magnitude of current being applied at Electrode 2 (as part of biphasic pulse 704-2). As depicted in FIG. 7A, the first positive magnitude may be substantially equal in magnitude to the first negative magnitude. Following the first phase (e.g., immediately following or after a short time), concurrent pulse 704 may further include a second phase of duration 706-2 in which a second negative magnitude of current is applied at Electrode 1 (as part of biphasic pulse 704-1) concurrently with a second positive magnitude of current being applied at Electrode 2 (as part of biphasic pulse 704-2). As depicted in FIG. 7A, the second negative magnitude may be substantially equal in magnitude to the second positive magnitude. Additionally, in some examples, the second positive and negative magnitudes may be substantially equal to the first positive and negative magnitudes, respectively, and duration 706-1 may be substantially equal to duration 706-2. In other examples, the second positive and negative magnitudes, while substantially equal to one another, may be different from the first positive and negative magnitudes, respectively. Additionally, in some examples, duration 706-1 may be different from duration 706-2.

While biphasic pulses such as pulses 704-1 and 704-2 may be convenient for the cochlear implant to generate and apply (e.g., because biphasic stimulation pulses may be used to stimulate the patient during normal operation of the cochlear implant system), it will be understood that other types of pulses may be employed as may serve a particular implementation. For example, monophasic pulses, non-square pulses, and so forth may be used instead of biphasic square pulses in certain implementations.

System 300 may be configured to track the proximity of the electrode lead to the cochlear tissue in real time during an insertion procedure in which the electrode lead is being surgically inserted into the cochlea of the patient. For example, the tracking may be performed by automatically repeating, at regular intervals, the directing of the cochlear implant to apply the first and second pulses, the directing of the cochlear implant to detect the energy magnitude, and the determining of the proximity of the electrode lead to the cochlear tissue. To illustrate, FIG. 7A shows that concurrent pulses 702 may be applied in a series such that each pulse is separated by a time interval 708. For example, time interval 708 may be the same between each pair of adjacent pulses 702 such that pulses 702 are applied every few hundred microseconds, every few milliseconds, or the like. In this way, it may seem to a surgeon performing an insertion procedure on a human timescale that pulses are being applied (and proximity measurements are being performed) continuously. In some examples, different intervals 708 may be used between different pulses.

Referring to FIG. 7B, a series of detected pulses 710 represented as a series of voltage pulses represents the energy magnitude of the fields generated as a result of the application of concurrent pulses 702 and as detected by an electrode referred to as "Electrode 3." It will be understood that the timeline depicted in FIG. 7B may align with the timeline of FIG. 7A such that each detected pulse 710 may correspond to a particular concurrent pulse 702 illustrated in FIG. 7A. In other words, for each concurrent pulse 702 that is applied, a corresponding detected pulse 710 may be detected to indicate the energy magnitude of the field (i.e., the field generated by the dipole formed by the application of the concurrent pulse 702) as the field reflects from tissue in the local volume of the field. For example, a detected pulse 712 may be detected based on the energy magnitude of the field generated as a result of the application of concurrent pulse 704, described above.

As shown in FIG. 7B, the first several detected pulses 710, including detected pulse 712, may be detected to have a similar magnitude (i.e., to represent a similar energy magnitude of the field). If these detected pulses are detected at a certain time within an insertion procedure (e.g., shortly after the distal tip of the electrode lead has entered the cochlea), system 300 may set this magnitude to be a baseline energy magnitude of the field. Accordingly, as long as pulses with the magnitude of detected pulse 712 are detected, system 300 may determine that the proximity of the electrode lead to the cochlear tissue is greater than a particular threshold distance. In other words, system 300 may determine that the electrode lead is not particularly proximate to the cochlear tissue.

As the series of pulses continues, however, system 300 may at some point detect a pulse that has either a smaller or a larger energy magnitude than the baseline energy magnitude of detected pulse 712. For example, as shown in FIG. 7B, system 300 may detect a detected pulse 714 with a relatively small energy magnitude as compared to the baseline energy magnitude of detected pulse 712, or a detected pulse 716 with a relatively large energy magnitude as compared to the baseline energy magnitude of detected pulse 712. Such changes in energy magnitude from the baseline energy magnitude may occur not because the field itself is being generated to have a different energy magnitude (note, for example, that the magnitude of concurrent pulses 702 in FIG. 7A does not change for the concurrent pulses 702 corresponding to detected pulses 714 and 716), but, rather, because of a change in how proximate Electrode 3 is to cochlear tissue (not shown in FIGS. 7A and 7B) when pulses 714 and 716 are detected.

Cochlear tissue encountered by a field generated within a cochlea may have a different effect on the field than cochlear fluid with which the field may interact when a baseline energy magnitude is determined. Moreover, as mentioned above, different types of cochlear tissue encountered by a field generated within a cochlea may also have different effects on the field. These effects may be represented in the magnitudes of detected pulses such as detected pulses 710. For example, an energy magnitude of a field may be detected to be decreased or diminished from the baseline if the electrode lead is proximate to soft or fleshy structures that reflect less field energy and/or absorb more field energy such as a basiliar membrane or the like. Conversely, an energy magnitude of a field may be detected to be increased or augmented from the baseline if the electrode lead is proximate to stiff or bony structures that reflect more field energy and/or absorb less field energy such as a lateral wall, a basiliar membrane, or the like.

FIGS. 8A and 8B illustrate exemplary movements of electrode lead 402 toward exemplary cochlear tissue. Specifically, as shown, electrode lead 402 may gradually become more proximate to cochlear tissue 802 by way of a lateral movement 804-L illustrated in FIG. 8A, or by way of a forward movement 804-F illustrated in FIG. 8B. Lateral movement 804-L and forward movement 804-F may be collectively referred to as movements 804. In FIGS. 8A and 8B, cochlear tissue 802 may represent any cochlear structure or any other suitable tissue that may interact with a field generated by a dipole formed by electrodes on electrode lead 402. For example, cochlear tissue 802 may represent a relatively bony structure that reflects field energy of a field generated in close proximity to the tissue such that a relatively high energy magnitude of the field may be detected as movements 804 occur.

FIG. 8C illustrates an exemplary graph depicting field energy magnitude detected as a function of the distance of electrode lead 402 from cochlear tissue 802 for movements 804-L and 804-F in a configuration in which the two most distal stimulating electrodes (i.e., electrodes 506-1 and 506-2) implement the first and second electrodes that form the dipole, and in which a sensing electrode at the distal tip (i.e., electrode 508) implements the third electrode that detects the field energy magnitude. It will be understood that the first and second electrodes forming the dipole that generates the field, as well as the third electrode for detecting the energy magnitude of the field, may be implemented by different configurations of the electrodes of electrode lead 402 to achieve different results than illustrated in FIG. 8C.

In FIG. 8C, a curve 806-L and a curve 806-F represent the energy magnitude detected for the field formed by a dipole between electrodes 506-1 and 506-2 as movements 804-L and 804-F occur, respectively. Specifically, starting from the right-hand side of curves 806-L and 806-F, where electrode lead 402 is within a proximity range 808 (i.e., at a relatively great distance from cochlear tissue 802), curves 806-L and 806-F illustrate relatively flat field energy magnitudes. This is because, regardless of the type of movement 804 that is taking place, the field generated by the dipole formed by electrode lead 402 may not significantly interact with cochlear tissue 802 at the relatively far distance of proximity range 808. As such, the field energy magnitude detected for electrode lead 402 while curves 806-L and 806-F are flat may be set to be a baseline energy magnitude against which further detected energy magnitude levels may be compared.

As illustrated by the behavior of curves 806-L and 806-F corresponding to a proximity range 810, field interactions (e.g., energy reflection from the tissue) may cause the detected field energy magnitude to dramatically slope upwards as compared to the flat baseline energy magnitude corresponding to proximity range 808. Such interaction may occur as electrode lead 402 becomes increasingly proximate to cochlear tissue 802 (i.e., as movements 804-L and 804-F occur). As shown, as curves 806-L and 806-F begin to slope upwards from the baseline energy magnitude to significantly higher energy magnitudes within proximity range 810, a predetermined threshold 812 from the baseline energy magnitude of the field may be crossed. For example, threshold 812 may be predetermined based on earlier calibration of system 300 or may be dynamically predetermined in an early stage of movements 804 when electrode lead 402 is within proximity range 808 and the baseline energy magnitude is being detected.

System 300 may use threshold 812 to determine the proximity of electrode lead 402 to cochlear tissue 802. For instance, the baseline energy magnitude of the field (i.e., the energy magnitude detected for curves 806-L and/or 806-F when the curves are substantially flat within proximity range 808) may be representative of an energy magnitude of the field in an absence of reflections of the field from cochlear tissue 802 (i.e., because sensing electrode 508 is not yet within proximity range 810). System 300 may then determine the proximity of electrode lead 402 to cochlear tissue 802 by determining that the difference between the detected energy magnitude of the field is greater than threshold 812 and by determining (e.g., based on the determination that the difference is greater than threshold 812) that sensing electrode 508 is within proximity range 810 of cochlear tissue 802.

In some implementations, system 300 may detect the proximity of electrode lead 402 to cochlear tissue 802 as a binary value. For example, when curves 806-L or 806-F remains below threshold 812, system 300 may determine that electrode lead 402 is not particularly proximate to cochlear tissue 802, whereas, when either curve rises above threshold 812, system 300 may determine that electrode lead 402 is in close proximity to cochlear tissue 802 and that a warning notification or the like should be issued. In other implementations, system 300 may detect and provide a more specific proximity value. For instance, as one example, various levels of proximity (e.g., "in range," "proximate," "very proximate," "touching," etc.) may be defined and detected based on the value of detected energy magnitude for electrode lead 402 and one or more predefined curve such as curves 806-L and 806-F. As another example, the proximity may be determined as a distance (e.g., in millimeters or other suitable distance units).

As illustrated by curves 806-L and 806-F, the geometry of detecting the proximity of electrode lead 402 to cochlear tissue 802 may be different for movement 804-L and for movement 804-F. For example, because the dipole generated between electrodes 506-1 and 506-2 may be able to get physically closer to cochlear tissue 802 with lateral movement 804-L than with forward movement 804-F, lateral movement 804-L may ultimately result in more field energy being reflected and FIG. 8C illustrates that curve 806-L may thus rise more steeply to achieve a greater field energy magnitude than curve 806-F. In some examples, along with determining the proximity of electrode lead 402 to cochlear tissue 802, system 300 may be calibrated to determine what type of movement 804 may be occurring based on the shape of the curve being detected (e.g., whether the curve is shaped like curve 806-L, curve 806-F, or something in between that may represent a movement with both lateral and forward components).

In certain implementations, system 300 may also be configured to determine the type of movement 804 (e.g., an angle of approach of electrode lead 402 to cochlear tissue 802) based on the baseline energy magnitude. For example, system 300 may determine, based on a difference between a detected energy magnitude of the field and at least one predetermined energy magnitude threshold, an electrode lead approach status within the cochlea and with respect to a modiolus of the cochlea.

Figure 9A:
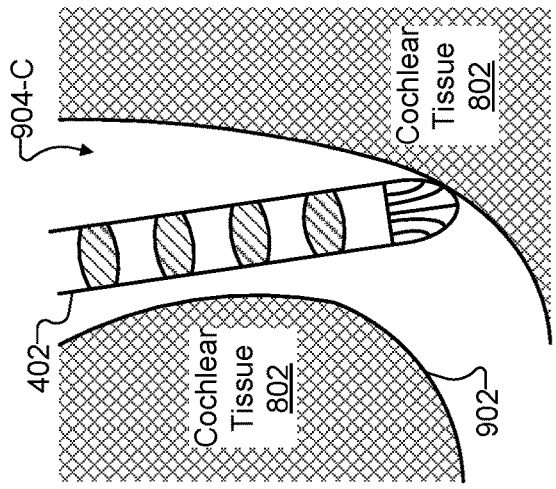
FIGS. 9A through 9C illustrate exemplary electrode lead approach statuses within an exemplary cochlea with respect to a modiolus of the cochlea according to principles described herein.
Figure 9B:
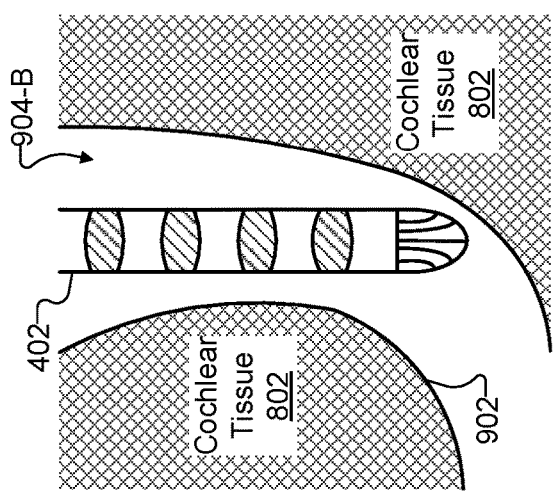
Figure 9C:
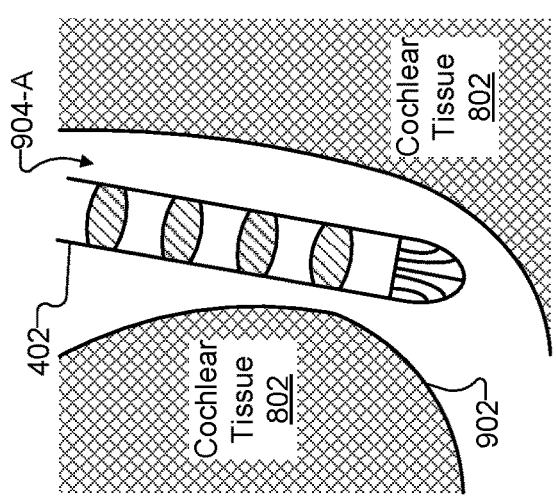

To illustrate, FIGS. 9A through 9C illustrate exemplary electrode lead approach statuses within an exemplary cochlea (e.g., cochlea 200) with respect to a modiolus 902 of the cochlea. Specifically, FIG. 9A illustrates an approach status 904-A in which the insertion of electrode lead 402 into the cochlea is angled toward modiolus 902, FIG. 9B illustrates an approach status 904-B in which the insertion of electrode lead 402 into the cochlea is straight (i.e., not angled toward or away from modiolus 902), and FIG. 9C illustrates an approach status 904-C in which the insertion of electrode lead 402 into the cochlea is angled away from modiolus 902. Approach statuses 904-A, 904-B, and 904-C may be collectively referred to herein as approach statuses 904.

Figure 9D:
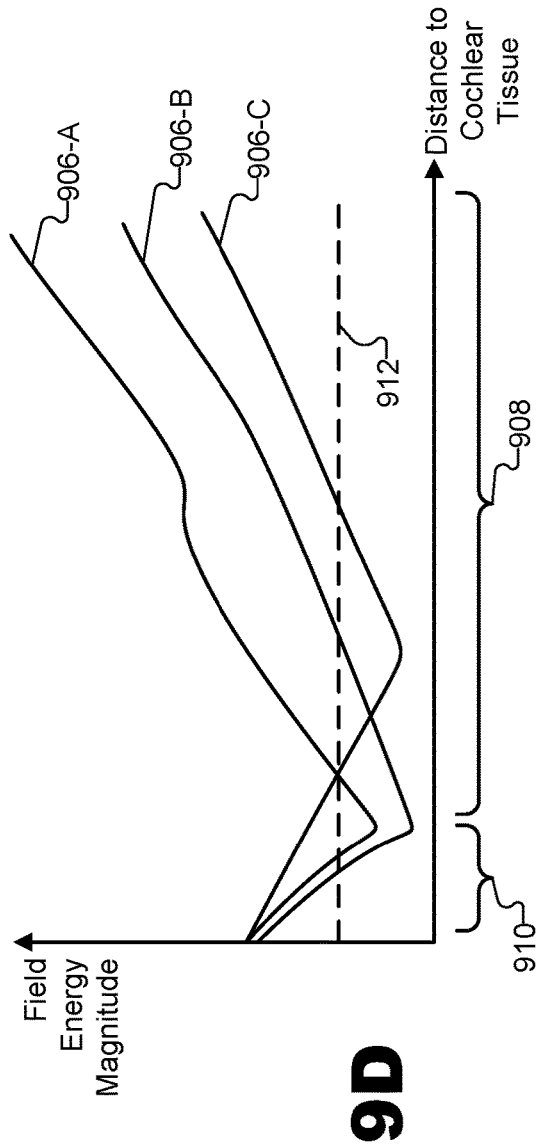
FIG. 9D illustrates an exemplary graph depicting field energy magnitude detected as a function of the proximity of the electrode lead to the cochlear tissue for the electrode lead approach statuses depicted in FIGS. 9A through 9C according to principles described herein.

FIG. 9D illustrates an exemplary graph depicting the field energy magnitude detected as a function of the distance of electrode lead 402 to cochlear tissue 802 for approach statuses 904. Specifically, FIG. 9D depicts a plurality of curves 906 (i.e., curves 906-A, 906-B, and 906-C) representative of the different approach statuses 904 (i.e., approach statuses 904-A, 904-B, and 904-C, respectively). The graph of FIG. 9D has much in common with the graph of FIG. 8C, described above. For example, FIG. 9D illustrates a proximity range 908 and a proximity range 910 that correspond to proximity ranges 808 and 810 of FIG. 8C, respectively, as well as a predetermined energy magnitude threshold 912 that corresponds to threshold 812. However, it will be noted that curves 906 have a different shape than curves 806. Specifically, while curves 806 in FIG. 8C are essentially flat within proximity range 808 (i.e., the field energy magnitude remains substantially constant as the distance between electrode lead 402 and cochlear tissue 802 decreases), curves 906 in FIG. 9D slope downward within proximity range 908 (i.e., the field energy magnitude decreases as the distance between electrode lead 402 and cochlear tissue 802 decreases).

These or other shapes of curves may be observed in different scenarios such as when electrode lead 402 is moving past or passing through different types of cochlear tissue, different shapes of cochlear structures, or the like. For example, one difference between FIGS. 8A-8B and FIGS. 9A-9C is that cochlear tissue 802 was only located on one side of electrode lead 402 in FIGS. 8A-8B, while in FIGS. 9A-9C, cochlear tissue 802 is located on both sides of electrode lead 402, thus causing more complex field interactions. Regardless of the slope of curves when electrode lead 402 is relatively far away from cochlear tissue 802, however, it is noted that the slope may abruptly change (e.g., from flat to sloping upward, from sloping downward to sloping upward, etc.) when electrode lead 402 gets relatively close to cochlear tissue 802. For example, just as curves 806 began sloping upward in proximity range 810 in FIG. 8C, curves 906 are shown to begin sloping upward as the distance decreases from proximity range 908 to proximity range 910 in FIG. 9D.

Accordingly, the baseline energy magnitude in certain examples may be represented as a constant energy magnitude value (i.e., associated with zero slope), while, in other examples, the baseline energy magnitude may be represented as a linear energy magnitude (i.e., associated with a particular slope) or with another suitable nonlinear shape. In other words, in the examples of curves 906, the proximity of electrode lead 402 may be determined to be relatively large (i.e., far away) as long as the slope of curves 906 are decreasing at a certain rate, and then the proximity may be determined to be relatively close when the slope of curves 906 change (e.g., flatten out or begin decreasing).

Depending on the energy magnitude detected for electrode lead 402 at a certain proximity or a certain location (e.g., right inside the round window at the entrance to the cochlea), system 300 may determine which type of approach status 904 electrode lead 402 may be taking. For example, system 300 may determine that there is a relatively large energy magnitude of the field detected inside the round window (i.e., such as illustrated by curve 906-A), thereby indicating an approach status toward modiolus 902 (i.e., such as illustrated by approach status 904-A). As another example, system 300 may determine that there is a moderate energy magnitude of the field detected inside the round window (i.e., such as illustrated by curve 906-B), thereby indicating a straight approach with respect to modiolus 902 (i.e., such as illustrated by approach status 904-B). As yet another example, system 300 may determine that there is a relatively small energy magnitude of the field detected inside the round window (i.e., such as illustrated by curve 906-C), thereby indicating an approach status away from modiolus 902 (i.e., such as illustrated by approach status 904-C). Different thresholds defined to resemble the different baselines illustrated by curves 906 may be used to determine what type of approach status electrode 402 may have for a given insertion procedure.

Figure 10:
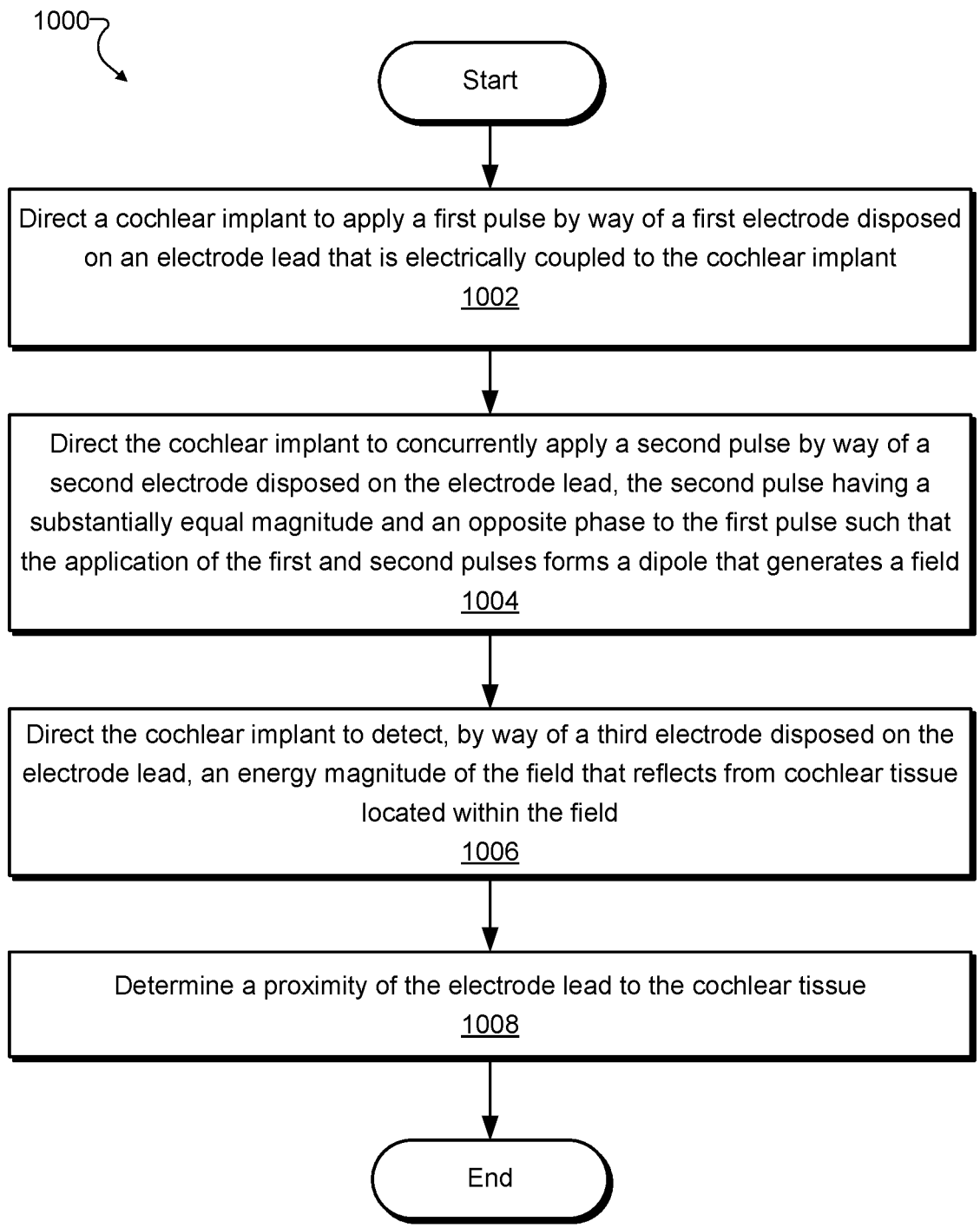
FIG. 10 illustrates an exemplary method for detecting electrode lead proximity to cochlear tissue according to principles described herein.

FIG. 10 illustrates an exemplary method 1000 for detecting electrode lead proximity to cochlear tissue. One or more of the operations shown in FIG. 10 may be performed by proximity detection system 300 and/or any implementation thereof. For example, method 1000 may be performed by a sound processor included within a cochlear implant system. While FIG. 10 illustrates exemplary operations according to one embodiment, other embodiments may omit, add to, reorder, and/or modify any of the operations shown in FIG. 10.

In operation 1002, a proximity detection system associated with a cochlear implant system may direct a cochlear implant to apply a first pulse. For example, the proximity detection system may direct the cochlear implant to apply the first pulse by way of a first electrode disposed on an electrode lead that is electrically coupled to the cochlear implant and is configured to be inserted into a cochlea of a patient. Operation 1002 may be performed in any of the ways described herein.

In operation 1004, the proximity detection system may direct the cochlear implant to apply a second pulse. For example, the application of the second pulse in operation 1004 may be performed concurrently with the application of the first pulse in operation 1002. The proximity detection system may direct the cochlear implant to apply the second pulse by way of a second electrode disposed on the electrode lead. In some examples, the second pulse may have a substantially equal magnitude and an opposite phase to the first pulse applied in operation 1002. As such, the application of the first and second pulses in operations 1002 and 1004 may form a dipole that generates a field. Operation 1004 may be performed in any of the ways described herein.

In operation 1006, the proximity detection system may direct the cochlear implant to detect an energy magnitude of the field that reflects from cochlear tissue located within the field. For example, the proximity detection system may direct the cochlear implant to detect the energy magnitude of the field by way of a third electrode disposed on the electrode lead. Operation 1006 may be performed in any of the ways described herein.

In operation 1008, the proximity detection system may determine a proximity of the electrode lead to the cochlear tissue. For example, the proximity detection system may determine the proximity of the electrode lead to the cochlear tissue based on a difference between the energy magnitude of the field detected in operation 1006 and a baseline energy magnitude of the field. Operation 1008 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
one or more processors communicatively coupled to the memory and configured to execute the instructions to perform a process comprising:
   directing a first electrode of an electrode lead to apply a first pulse;
   directing a second electrode of the electrode lead to apply a second pulse concurrently with the first pulse so as to form a dipole that generates a field; and
   determining, based on an energy magnitude of the field that is detected by a third electrode to reflect from cochlear tissue located within the field, a proximity of the electrode lead to the cochlear tissue;
wherein the first and second electrodes are each configured as stimulating electrodes that apply stimulation to the cochlear tissue when the electrode lead is located at a resting position subsequent to a surgical insertion of the electrode lead into a cochlea of a patient.

2. The system of claim 1, wherein:
the memory and the one or more processors are implemented within a sound processor communicating with a cochlear implant to which the electrode lead is coupled;
the first and second pulses are current pulses generated by a current source included within the cochlear implant;
the dipole formed by the first and second pulses is an electric dipole; and
the field generated by the dipole is an electric field.

3. The system of claim 1, wherein:
the process further comprises directing the third electrode to detect the energy magnitude of the field that reflects from the cochlear tissue;
the third electrode is disposed at a distal-most electrode position on the electrode lead; and
the first and second electrodes are disposed at electrode positions more distal than any other electrode positions besides the distal-most electrode position.

4. The system of claim 3, wherein:
the distal-most electrode position at which the third electrode is disposed is a distal-most tip of the electrode lead; and
the third electrode is implemented as a sensing electrode that is configured to detect the energy magnitude of the field and does not apply stimulation to the cochlear tissue when the electrode lead is located at the resting position subsequent to the surgical insertion of the electrode lead.

5. The system of claim 1, wherein an electrode other than the first, second, or third electrodes is disposed on the electrode lead at a distal-most electrode position on the electrode lead.

6. The system of claim 1, wherein the first and second electrodes are disposed at adjacent electrode positions on the electrode lead.

7. The system of claim 1, wherein:
the second pulse has a substantially equal magnitude and an opposite phase to the first pulse; and
the first and second pulses are biphasic current pulses each including:
   a first phase in which a first positive magnitude of current is applied at the first electrode concurrently with a first negative magnitude of current being applied at the second electrode, and
   a second phase in which a second negative magnitude of current is applied at the first electrode concurrently with a second positive magnitude of current being applied at the second electrode.

8. The system of claim 1, wherein the process further comprises tracking the proximity of the electrode lead to the cochlear tissue during the surgical insertion of the electrode lead into the cochlea.

9. The system of claim 1, wherein the process further comprises directing the third electrode to detect the energy magnitude of the field that reflects from the cochlear tissue by detecting a voltage between the third electrode and a ground reference.

10. The system of claim 1, wherein the process further comprises directing the third electrode to detect the energy magnitude of the field that reflects from the cochlear tissue by detecting a voltage between the third electrode and a fourth electrode of the electrode lead, the fourth electrode configured as a stimulating electrode that applies stimulation to the cochlear tissue when the electrode lead is located at the resting position subsequent to the surgical insertion of the electrode lead into the cochlea.

11. The system of claim 1, wherein:
the determining of the proximity of the electrode lead to the cochlear tissue is performed based on a difference between:
   the energy magnitude of the field detected by the third electrode to reflect from the cochlear tissue located within the field, and
   a baseline energy magnitude of the field that is representative of an energy magnitude of the field in an absence of reflections of the field from cochlear tissue within a predetermined proximity of the third electrode; and
the determining of the proximity of the electrode lead to the cochlear tissue includes determining that the third electrode is within a predetermined proximity of the cochlear tissue based on a determination that the difference is greater than a predetermined threshold.

12. The system of claim 1, wherein:
the determining of the proximity of the electrode lead to the cochlear tissue is performed based on a difference between:
   the energy magnitude of the field detected by the third electrode to reflect from the cochlear tissue located within the field, and
   a baseline energy magnitude of the field that is representative of an energy magnitude of the field in an absence of reflections of the field from cochlear tissue within a predetermined proximity of the third electrode; and
the determining of the proximity of the electrode lead to the cochlear tissue includes determining an electrode lead approach status within the cochlea and with respect to a modiolus of the cochlea based on a determination that the difference is greater than at least one predetermined energy magnitude threshold.

13. The system of claim 1, wherein:
the directing of the first electrode to apply the first pulse, the directing of the second electrode to apply the second pulse, and the determining of the proximity of the electrode lead to the cochlear tissue are all performed during the surgical insertion of the electrode lead into the cochlea; and
the process further comprises providing, during the surgical insertion of the electrode lead into the cochlea and based on the determined proximity of the electrode lead to the cochlear tissue, real-time feedback to a user associated with performing the surgical insertion of the electrode lead into the cochlea.

14. The system of claim 1, wherein:
the directing of the first electrode to apply the first pulse, the directing of the second electrode to apply the second pulse, and the determining of the proximity of the electrode lead to the cochlear tissue are all performed when the electrode lead is located at the resting position subsequent to the surgical insertion of the electrode lead into the cochlea; and
the process further comprises providing, subsequent to the surgical insertion of the electrode lead into the cochlea and based on the determined proximity of the electrode lead to the cochlear tissue, data indicative of the resting position of the electrode lead within the cochlea.

15. The system of claim 14, wherein an electrode other than the first, second, or third electrodes is disposed on the electrode lead at a distal-most electrode position on the electrode lead.

16. The system of claim 1, wherein:
the third electrode is implemented as a sensing electrode that is configured to detect the energy magnitude of the field and does not apply stimulation to the cochlear tissue when the electrode lead is located at the resting position subsequent to the surgical insertion of the electrode lead; and
the third electrode shares a common feedthrough conductor with a fourth electrode that is configured as a stimulating electrode that applies stimulation to the cochlear tissue when the electrode lead is located at the resting position subsequent to the surgical insertion of the electrode lead into the cochlea.

17. A cochlear implant system comprising:
an electrode lead configured to be surgically inserted into a cochlea of a patient, the electrode lead including:
   a first electrode and a second electrode that are each configured as stimulating electrodes that apply stimulation to cochlear tissue within the cochlea when the electrode lead is located at a resting position subsequent to surgical insertion of the electrode lead into the cochlea, and
   a third electrode that is configured to detect an energy magnitude of a field that reflects from cochlear tissue located within the field;
a cochlear implant configured to be implanted within the patient and coupled with the electrode lead, the cochlear implant further configured to concurrently apply a first pulse by way of the first electrode and a second pulse by way of the second electrode to form a dipole that generates the field; and
a sound processor communicatively coupled with the cochlear implant and configured to:
   direct the cochlear implant to concurrently apply the first and second pulses,
   detect the energy magnitude of the field using the third electrode, and
   determine, based on the detected energy magnitude of the field, a proximity of the electrode lead to the cochlear tissue.

18. The cochlear implant system of claim 17, wherein:
the second pulse has a substantially equal magnitude and an opposite phase to the first pulse; and
the first and second pulses are biphasic current pulses each including:
   a first phase in which a first positive magnitude of current is applied at the first electrode concurrently with a first negative magnitude of current being applied at the second electrode, and
   a second phase in which a second negative magnitude of current is applied at the first electrode concurrently with a second positive magnitude of current being applied at the second electrode.

19. The cochlear implant system of claim 17, wherein:
the determining of the proximity of the electrode lead to the cochlear tissue is performed based on a difference between:
   the energy magnitude of the field detected using the third electrode, and
   a baseline energy magnitude of the field that is representative of an energy magnitude of the field in an absence of reflections of the field from cochlear tissue within a predetermined proximity of the third electrode; and
the determining of the proximity of the electrode lead to the cochlear tissue includes determining that the third electrode is within a predetermined proximity of the cochlear tissue based on a determination that the difference is greater than a predetermined threshold.

20. A method comprising:
directing a first electrode of an electrode lead to apply a first pulse;
directing a second electrode of the electrode lead to apply a second pulse concurrently with the first pulse so as to form a dipole that generates a field; and
determining, based on an energy magnitude of the field that is detected by a third electrode to reflect from cochlear tissue located within the field, a proximity of the electrode lead to the cochlear tissue;

wherein the first and second electrodes are each configured as stimulating electrodes that apply stimulation to the cochlear tissue when the electrode lead is located at a resting position subsequent to a surgical insertion of the electrode lead into a cochlea of a patient.

\* \* \* \* \*